(12) United States Patent
Kirschner

(10) Patent No.: US 12,016,962 B2
(45) Date of Patent: Jun. 25, 2024

(54) UV EQUIPPED SMART HAIR APPLIANCE ORGANIZER THAT IS EITHER WALL MOUNTED OR A TRAVEL CADDY

(71) Applicant: Jeffrey Kirschner, Santa Clarita, CA (US)

(72) Inventor: Jeffrey Kirschner, Santa Clarita, CA (US)

(73) Assignee: Stylerbox Inc., Santa Clarita, CA (US)

( * ) Notice: Subject to any disclaimer, the term of this patent is extended or adjusted under 35 U.S.C. 154(b) by 833 days.

(21) Appl. No.: 17/151,141

(22) Filed: Jan. 16, 2021

(65) Prior Publication Data

US 2021/0322591 A1 Oct. 21, 2021

Related U.S. Application Data

(63) Continuation-in-part of application No. 16/868,115, filed on May 6, 2020, now abandoned.

(60) Provisional application No. 63/012,610, filed on Apr. 20, 2020.

(51) Int. Cl.
*A61L 2/10* (2006.01)
*A45D 44/04* (2006.01)

(52) U.S. Cl.
CPC ............. *A61L 2/10* (2013.01); *A45D 44/04* (2013.01); *A61L 2202/11* (2013.01); *A61L 2202/121* (2013.01); *A61L 2202/14* (2013.01)

(58) Field of Classification Search
CPC ........................................................ A61L 2/10
See application file for complete search history.

(56) References Cited

U.S. PATENT DOCUMENTS

| 5,029,252 A * | 7/1991 | Ameseder ................ A61L 2/10 |
| | | 250/455.11 |
| 9,669,122 B1 * | 6/2017 | Cruz-Acosta ......... A45D 44/00 |
| 2003/0222069 A1 * | 12/2003 | Sena ..................... A45D 20/12 |
| | | 219/222 |
| 2007/0283978 A1 * | 12/2007 | Montagnino ........... A45D 1/04 |
| | | 132/211 |

FOREIGN PATENT DOCUMENTS

WO    WO-2009065128 A2 *   5/2009   ............. A61L 2/10

* cited by examiner

*Primary Examiner* — Donald R Spamer
(74) *Attorney, Agent, or Firm* — Karthik Murthy; Murthy Patent Law Inc.

(57) ABSTRACT

In one embodiment of the present invention, there is an ultraviolet equipped smart hair appliance organizer ("organizer") that can be mounted on a wall or taken off the wall and closed with a lid for portability. Both the lid and a front plate contain sanitization and disinfecting lights that shine ultraviolet light on hair appliances. The organizer has coiled cords connecting the hair appliances. The organizer utilizes lasers in order to detect the presence of hair appliances within the organizer; automatically shut off the hair appliances after a preset time period of the hair appliances being inside the organizer; automatically turn on ultraviolet lights for the purpose of sanitization and disinfection of the hair appliances inside the organizer as soon as the organizer is closed; and automatically shut off the ultraviolet lights after a preset time period.

6 Claims, 22 Drawing Sheets

103

UV EQUIPPED SMART HAIR APPLIANCE ORGANIZER THAT IS EITHER WALL MOUNTED OR A TRAVEL CADDY

CROSS-REFERENCE TO RELATED APPLICATION

This application is a continuation of U.S. patent application Ser. No. 16/868,115, filed May 6, 2020, which claims priority from Provisional U.S. application Ser. No. 63/012,610, filed Apr. 20, 2020, and the disclosure of both applications is hereby incorporated by reference herein in its entirety

FIELD OF THE INVENTION

The present invention relates to a UV-C equipped smart hair appliance organizer that is either wall mounted or a travel caddy that utilizes ultraviolet light to sanitize and disinfect hair appliances, as well as sterilize hair appliances and hair tools accessories such as hair clips, combs, shears, hair brushes, make up brushes, cell phone and keys.

BACKGROUND

The background description includes information that may be useful in understanding the present invention. It is not an admission that any of the information provided herein is prior art or relevant to the presently claimed invention, or that any publication specifically or implicitly referenced is prior art.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. The following description includes information that may be useful in understanding the present invention. It is not an admission that any of the information provided herein is prior art or relevant to the presently claimed invention, or that any publication specifically or implicitly referenced is prior art.

In some embodiments, the numbers expressing quantities of ingredients, properties Such as concentration, reaction conditions, and so forth, used to describe and claim certain embodiments of the invention are to be understood as being modified in some instances by the term "about."

Accordingly, in some embodiments, the numerical parameters set forth in the written description and attached claims are approximations that can vary depending upon the desired properties sought to be obtained by a particular embodiment.

In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an and "the includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "Such as") provided with respect to certain embodiments herein is intended merely to better illuminate the invention d does not pose a limitation on the scope of the invention otherwise claimed.

No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When Such inclusion or deletion occurs, the specification is herein deemed to contain the group as modified thus fulfilling the written description of all Markush groups used in the appended claims.

Today, people in hotel rooms can be inclined to leave appliances on, because they're not paying the electric bill. This can cause overheating in the appliances, as well as damage to the appliances and to the surrounding area. Another problem it can cause is that the hair appliances might run out of power, or stay on too long while consuming power unnecessarily.

Also, the coronavirus epidemic has instilled in people a serious concern about germs and bacteria that people may not have felt before. The coronavirus has been found to be able to survive for several hours on surfaces. As such, people may be very concerned about what they touch, and what objects touch them.

Therefore, people might be concerned about germs and bacteria on hair appliances, especially during and after the coronavirus pandemic. They don't know whether hair appliances have been properly cleaned after that last visitor to a hotel room used them.

Also, if a hair stylist visits a customer in their home, the customer doesn't know if the hair stylist's hair appliances are clean. Or if the customer goes to a hair salon, the customer again doesn't know if the bar salon's hair appliances are clean.

SUMMARY

The present invention provides a UV equipped smart hair appliance organizer that is either wall mounted or a travel caddy, and it is a combination of solving the issues mentioned above for the most common hair appliances. The present invention is very convenient for a user of hair appliances, because the power levels of the hair appliances can be controlled and administered when the hair appliances, such as a curling iron, flat iron and hair dryer, are connected to the UV equipped smart hair appliance organizer that is either wall mounted or a travel caddy. After being placed in the UV equipped smart hair appliance organizer that is either wall mounted or a travel caddy, the hair appliances are automatically disinfected so that they can be ready for the user to use again on a new person.

In another embodiment, the present invention provides a UV-C equipped smart hair appliance organizer that is either wall mounted or a travel caddy, and it is a combination of solving the issues mentioned above for the most common hair appliances. The present invention is very convenient for a user of hair appliances, because the power levels of the hair appliances can be controlled and administered when the hair appliances, such as a curling iron, flat iron and hair dryer, are connected to the UV-C equipped smart hair appliance organizer that is either wall mounted or a travel caddy. After being placed in the UV-C equipped smart hair appliance organizer that is either wall mounted or a travel caddy, the hair appliances and hair tools accessories such as hair clips, combs, shears, hair brushes, make up brushes, cell phone and keys are automatically sterilized so that they can be ready for the user to use again on a new person.

During the coronavirus pandemic, and likely forever afterwards, people will be increasingly concerned about germs from other people who may have been infected. This is a great solution to that problem, because the invention disinfects the hair appliances and sterilizes the hair appliances and also sterilizes hair tools accessories such as hair clips, combs, shears, hair brushes, make up brushes, cell phone and keys, so as to help prevent the spread of the coronavirus or other viruses. The person receiving treatment will not want germs from another person on the hair appliances that will be touching their body.

The present invention also solves multiple problems for hotels, professional stylists and cosmetologists, because the present invention utilizes ultraviolet light to disinfect and sanitize hair appliances. This ensures that the next person to stay in the hotel, or the next client that sits in the chair of a cosmetologist or the service chair of a stylist, will have a lower likelihood of getting contaminated with coronavirus, or hopefully anything else, by touching the hair appliances. This is because the sanitary and disinfection processes destroy various germs, harmful bacteria and possibly viruses that might reside on the hair appliances.

In another embodiment, the present invention also solves multiple problems for hotels, professional stylists and cosmetologists, because the present invention utilizes Premium Ultraviolet light called UV-C light to sterilize hair appliances and hair tools accessories such as hair clips, combs, shears, hair brushes, make up brushes, cell phone and keys. This ensures that the next person to stay in the hotel, or the next client that sits in the chair of a cosmetologist or the service chair of a stylist, will have a lower likelihood of getting contaminated with coronavirus, or hopefully anything else, by touching the hair appliances or the hair tools accessories. This is because the sterilization processes destroys various germs, harmful bacteria and possibly viruses that might reside on the hair appliances.

The ultraviolet light and premium ultraviolet UV-C light known as UV-C light also destroys viruses in general. As such, hair stylists in hair salons and hair stylists going to a customer's home can utilize the present invention's ultraviolet light to destroy viruses, as well as germs and bacteria, in order to put the customer at ease and to not actually contaminate the customer.

The present invention also solves the power problem by utilizing an auto shut off system. This system automatically shuts off power to the appliances based on a preset timer when the hair appliances are left outside of a case. Alternatively, the system automatically shuts off power to the appliances and recharges the appliances once the appliances are put back in a case that is designed to disinfect, sanitize and power the hair appliances.

In another embodiment of the present invention, it solves the power supply problem by utilizing an innovative auto shut off system for the Flat Iron and Curling Iron based on a preset timer of 1 hour auto shut off for our hotel model, and 2 hour auto shut off for our professional stylist model and retail model. And uses an innovative immediate shut off for the Blow dryer, when the blow dryer is placed inside the unit allowing the professional stylist to have immediate power down of the blow dryer for convenience when working on a client's hair. This saves time for the stylist, creates convenience, conserves life of the blow dryer, and our unit is the only product on the market to perform this function. This system automatically shuts off power to all appliances based on a preset timer when the hair appliances are also left outside of a the unit. Alternatively, once the appliances are pulled back out of the unit for use, the power resumes immediately to all hair appliances allowing for the hotel guest, professional cosmetologist and retail at home user to use the hair appliances once again.

DESCRIPTION OF THE DRAWINGS

Many aspects of the present disclosure can be better understood with reference to the attached drawings. The components in the drawings are not necessarily drawn to scale, with emphasis instead being placed upon clearly illustrating the principles of the disclosure. Moreover, in the drawings, like reference numerals designate corresponding parts throughout several views.

SPECIFICATION

Figure 1A:
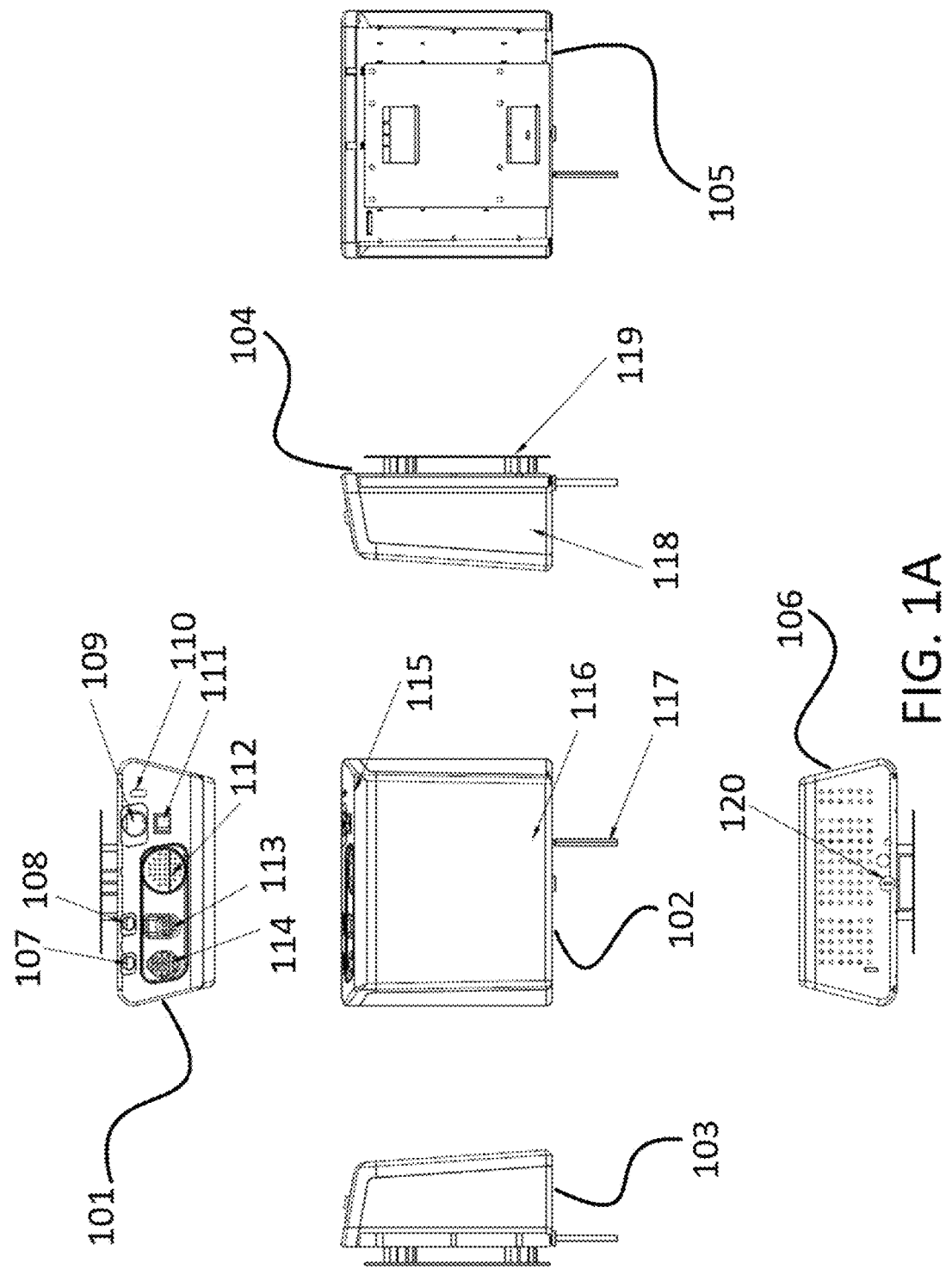
FIG. 1A is the schematic view of one embodiment of the UV-C light equipped smart hair appliance organizer that is either wall mounted or a travel caddy according to various embodiments of the present disclosure.

The present invention is a system for a UV-C light equipped smart hair appliance organizer that is either wall mounted or a travel caddy. The invention can house beauty hair appliances and hair accessory tools such as clips, combs, shears, hair brushes, make up brushes, keys and a cell phone. The invention also protects the health of users and commercial businesses through a system that offers light sanitization and disinfection of the beauty hair appliances. In another embodiment, the system offers light sterilization of the beauty hair appliances and hair accessory tools such as clips, combs, shears, hair brushes, make up brushes, keys and a cell phone. Such beauty hair appliances include a flat iron, a curling iron, and a hair blow dryer.

One embodiment of the invention has an air cooling system to cool down a set of beauty hair appliances, including a flat iron, a curling iron, and a hair blow dryer. Another embodiment of the invention has an auto shut off system that shuts off all 3 beauty hair appliances when all 3 beauty hair appliances are placed back in the system.

The system detects the appliances by using a laser detection system that alerts a computer in the system to the presence of the appliances, and thereby triggers an automatic shut off of the appliances based on a preset timer, as well as charging the appliances and starting either a UV disinfection process or a UV-C light sterilization process.

Another embodiment of the invention includes turning off all 3 beauty hair appliances by a timer system when the beauty hair appliances are left outside of the system after a set amount of time. The system has the places to mount the hair appliances of a flat iron, curling iron, and hair dryer. When any of the hair appliances are taken out of the system, the hair appliances will function automatically for a certain period of time.

Alternatively, if the hair appliances are placed back into the system, the auto shut off system will automatically shut off the power to the curling iron, flat iron and hair blow dryer. A laser system detects when the hair appliances are placed in the system, and alerts a computer in the system to automatically shut off the appliances. Simultaneously, the light sanitization, disinfection and air fan cool down system will be triggered and turned on for a fixed amount of time so as to dry each of the hair appliances. In an alternative embodiment of the invention, the air fan cool down system is a high performance fan system for cooling down appliances.

In another alternative, if the hair appliances are placed back into the unit, the auto shut off system based on a preset timer will automatically shut off the power to the curling iron, flat iron and hair blow dryer. A laser system detects when the hair appliances are placed in the system, and alerts a computer in the system to automatically shut off the appliances. Simultaneously, the UV-C light sterilization and air fan cool down system will be triggered and turned on for a fixed amount of time so as to cool down each of the hair appliances. In an alternative embodiment of the invention, the air fan cool down system is a high performance fan system for cooling down appliances.

In another embodiment of the invention, light sanitization and disinfection is used to sanitize and disinfect the flat iron and curling iron, and an air fan system is used to cool down the flat iron, curling iron, and blow dryer. There is a timer for the light sanitization, disinfection and air fan so that these systems turn off after a set amount of time to preserve the life of these systems. When the timer runs out, the light sanitization, disinfection and air fan will stop automatically.

In another embodiment of the invention, light sterilization is used to sanitize and disinfect the flat iron and curling iron, and an air fan system is used to cool down the flat iron, curling iron. There is a timer for the UV-C light sterilization and air fan so that these systems turn off after a set amount of time to preserve the life of these systems. When the timer runs out, the light sanitization, disinfection and air fan will stop automatically.

In one embodiment of the invention, the light sanitization and disinfection that is performed is Ultraviolet germicidal irradiation (UVGI), which is a disinfection method that uses short-wavelength ultraviolet (ultraviolet C or UVC) light to kill or inactivate microorganisms by destroying nucleic acids and disrupting their DNA, leaving them unable to perform vital cellular functions. UVGI is used in a variety of applications, such as food, air, and water purification. This produces strong enough UVC light in circulating air or water systems to make them inhospitable environments to microorganisms such as bacteria, viruses, molds and other pathogens.

In one embodiment of the invention, the UV-C light sterilization that is performed is Ultraviolet germicidal irradiation (UVGI), which is a sterilization method that uses short-wavelength ultraviolet (ultraviolet C or UVC), light to kill or inactivate microorganisms by destroying nucleic acids and disrupting their DNA, leaving them unable to perform vital cellular functions. UVGI is used in a variety of applications, such as food, air, and water purification. This produces strong enough UVC light in circulating air or water systems to make them inhospitable environments to microorganisms such as bacteria, viruses, molds and other pathogens.

UV light is electromagnetic radiation with wavelengths shorter than visible light but longer than X-rays. UV can be separated into various ranges, with short-wavelength UV (UVC) considered "germicidal UV". Wavelengths between about 200 nm and 300 nm are strongly absorbed by nucleic acids. The absorbed energy can result in defects including pyrimidine dimers. These dimers can prevent replication or can prevent the expression of necessary proteins, resulting in the death or inactivation of the organism.

UV-C light is electromagnetic radiation with wavelengths shorter than visible light but longer than X-rays. UV-C light can be separated into various ranges, with short-wavelength UV (UVC) considered "germicidal UV-C". Wavelengths between about 100~275 nm are strongly absorbed by nucleic acids. The absorbed energy can result in defects including pyrimidine dimers. These dimers can prevent replication or can prevent the expression of necessary proteins, resulting in the death or inactivation of the organism. The UVC band wavelength is 100~275 nm, also known as short-wave sterilization. Ultraviolet penetration is weak, and cannot penetrate most transparent glass and plastic. Sunlight contains short-wave ultraviolet rays, and is almost completely absorbed by the ozone layer. Short-wave ultraviolet rays are harmful to the human body. Long-term or high-intensity burns. Irradiation can also cause skin cancer ultraviolet germicidal lamps to emit UVC short-wave ultraviolet rays. In another embodiment of the invention, a combination of UVC (260 nm-270 nm) for sterilizing and UVA (395 nm-405 nm) for auxiliary disinfection is effective.

Mercury-based lamps operating at low vapor pressure emit UV light at the 253.7 nm line. As such, in one embodiment of the invention, mercury based lamps are used for UV light.

Ultraviolet light-emitting diodes (UVC LED) lamps emit UV light at selectable wavelengths between 255 and 280 nm. As such, in one embodiment of the invention, UVC LED lamps are used for UV light.

Ultraviolet light-emitting diodes (UVC LED) lamps emit UV-C light at selectable wavelengths between 260 to 270 nm. As such, in one embodiment of the invention, UVC LED lamps are used for UV light.

Pulsed-xenon lamps emit UV light across the entire UV spectrum with a peak emission near 230 nm. As such, in one embodiment of the invention, pulsed-xenon lamps are used for UV light.

The effectiveness of germicidal UV depends on the length of time a microorganism is exposed to UV, the intensity and wavelength of the UV radiation, the presence of particles that can protect the microorganisms from UV, and a microorganism's ability to withstand UV during its exposure. As such, in one embodiment of the invention, the time that the hair appliances are exposed to UV light can be adjusted, it can be increased for additional effectiveness, or lowered if the user has limited time available.

The effectiveness of germicidal UV-C light depends on the length of time a microorganism is exposed to UV-C light, the intensity and wavelength of the UV-C radiation, the presence of particles that can protect the microorganisms from UV-C, and a microorganism's ability to withstand UV-C during its exposure. As such, in one embodiment of the invention, the time that the hair appliances are exposed to UV-C light can be adjusted, it can be increased for additional effectiveness, or lowered if the user has limited time available.

Lamp cooling under airflow can also lower output; thus, care should be taken to shield lamps from direct airflow, or to add additional lamps to compensate for the cooling effect. As such, the present invention maximizes UV light by functioning without direct airflow in encased space, because the system is in a case that prevents outside air flow.

Lamp cooling under airflow can also lower UV-C output thus, care should be taken to shield lamps from direct airflow, or to add additional lamps to compensate for the cooling effect. As such, the present invention maximizes UV-C light by functioning without direct airflow in an encased space, because the system is in a case that prevents outside air flow.

In one embodiment of the invention, coiled cords are connected to each of the appliances from the system, including, the flat iron, curling iron and hair dryer. Today there are no curling irons or flat irons that have coiled cords globally from any company on the market. Coiled cords would be useful in these devices because they prevent any slack in a loose cord, which might then be pulled by a child who might get injured by a hot curling iron or flat iron. Coiled cords would prevent any slack, and so a child would not have anything that they could reach to pull, and so the child would be safer than they otherwise would be. Coiled cords also prevent a child from ripping, the entire system out of the wall and injuring the child or anyone else. Coiled cords are a must have for the hotel accounts and residentials at home consumer accounts as they cannot have the standard 8 foot to 9 foot flat cords hanging on the bathroom counter and down to the floor for visual, cosmetic and liability reasons. These cords are also first to market in the hotel category, and the retail at home user market, and a main sales point in that both the hotel and retail residential at home user consumer. These coiled cords remove the mess that all homes have by long 8 foot to 9 foot standard flat cords produce. These coded cords solve that issue. These coiled cords were developed at a specific length to solve that visual problem for the hotel market and residential markets.

In another embodiment of the invention, the timing, charging and sanitary process is controlled by a computer built into the case, utilizing a processor, memory and storage for instructions on when to recharge, when to automatically shut off appliances that have been outside the case too long, how long to charge appliances when they are in the case, and when and how to run the UV light to sanitize and disinfect the hair appliances inside the case.

In another embodiment of the invention, the timing, charging and sterilization process is controlled by a computer built into the unit, utilizing a processor, memory and storage for instructions on when to recharge, when to automatically shut off appliances that have been outside the case too long, how long to charge appliances when they are in the case, and when and how to run the UV-C light to sterilize the hair appliances inside the unit.

In another embodiment of the invention, 2 forms of hair appliance auto shut off technology initiated and controlled by a laser and a timer. When the user puts the hair appliances back in the system, the system shuts the power off to the appliances based on a timer system. When you leave the appliances out of the system, the system will also shut the power off to the appliances based upon a timer system. This makes sure there are no appliances left running and unattended.

In another embodiment of the invention, the invention includes a first to market coiled corded flat iron and curling iron and blow dryer. The coiled cords attached to the Flat iron and Curling and blow dryer protects from long cords hanging in a bathroom which visually unattractive. It also protects against a child grabbing and pulling on the cords and potentially ripping the whole unit out of the wall and potentially hurting that child.

In another embodiment of the invention, the system's front plate is removable, and can be replaced by a screen expansion kit that customers can buy and install on their own. This new front plate which is called a Screen Expansion Kit allows paid advertisements to be played on the screen which we load from a corporate office, and the corporate office shares that advertising revenue with customers. It also allows for people to buy the appliances right from the Screen Expansion Kit, and those appliances will be shipped from a distribution center to that customer's doorstep. This will also be a part of a shared revenue model with customers.

In one embodiment of the invention, in which the invention is meant to be used in a hotel room, there are plugs to plug the hair appliances in for power. Those plugs are on the inside of the unit.

In another embodiment of the invention the system is as small as possible so as to make it convenient for the user to carry from location to location. This is more likely during the coronavirus pandemic as well, considering that hair salons have largely closed, so any such use of hair appliances will be in someone's home. This will eliminate the need for the user to go from someone's house to a place to disinfect their hair appliances, and then to the next house. Instead, the user can go from house to house, and be confident that the present invention has disinfected the hair appliances as well as recharged the hair appliances.

In another embodiment of the invention the system the cooling air fan has been removed, and the task of keeping the system cool is left to the user. This version is intended for personal retail consumption, because if only 1 or a limited number of individuals in a household is using the device, it is less likely to overheat in comparison to a version in constant use in a hotel.

In one embodiment of the invention, there is a retail model version of the system.

The retail model can be mounted on a user's home bathroom wall. At the push of a button, the retail model releases from that mounting system, thus allowing a user to travel with the retail model.

The retail model has a lid that secures the unit for travel, and has the UV lights for sanitization and disinfection in the lid and the front plate of the retail model. Also, just like other embodiments of the invention, the UV sanitization and disinfection lighting is located in the compartment containing the bottom half of the flat iron, curling iron and blow dryer, such that the UV sanitization and disinfection lighting sanitizes and disinfects the bottom half of the flat iron, curling iron and blow dryer.

In another embodiment, the retail model has a lid that secures the unit for travel, and has the UV-C lights for sterilization in the lid for the hotel, retail and professional model. Also, just like other embodiments of the invention, the UV-C sterilization lighting is located in the compartment containing the bottom half of the flat iron, curling iron and blow dryer, such that the UV-C sterilizes the bottom half of the flat iron, curling iron and blow dryer.

The retail model comes with a flat iron, curling iron and blow dryer. The retail model is equipped with first to market coiled cords. The coiled cords are attached to the curling iron, Flat Iron and Blow dryer. The coiled cords prevent the mess that normal hair appliance cords would create. This make the bathroom less cluttered, and much more visually appealing to the home owner. There are no coiled cords attached to hair appliances on the market at this time.

In another embodiment of the invention meant to be used in a hotel room, the plugs to plug the appliances in for power, are on the inside of the unit. In contrast, in the embodiment of the invention that is the retail model, the power outlets are cleverly placed facing the outside of the unit so the customer can plug and unplug the hair appliances at any time. This placement of the power outlets on the outside of the unit further allows the customer to replace the existing hair appliances with any other appliances that the customer chooses.

The retail model will also have an Auto shut off feature. The auto shut off feature functions such that when the Curling Iron, Flat Iron and Blow Dryer are placed back in the system, all of those appliances will automatically shut off after 1 hour. The auto shut off will also shut the appliances down when you close the lid of the system. The auto shut off also turns the appliances off when the appliances are left outside the box after 1 hour. The auto shut off system uses laser detection to detect the location and presence of the hair appliances.

The retail model also allows the front plate to the removable for future add ons and upgrades. The front plate is the same as the front cover or front plate of the system 116.

The retail model does not have a cool down fan system. This allows the size of the unit to be smaller, thus saving money on material to enclose the unit, and thus bringing the cost of the unit down for the consumer. The reduced size and lack of a cool down fan system also reduces the weight of the unit, thus leading to increased portability.

In one embodiment of the invention, there is a professional model.

The professional model is made to be a work horse unit for the professional stylist and cosmetologist. They will need to sanitize and disinfect all their hair appliances in between each client for state board and state regulations. Furthermore, during and after the time of the coronavirus pandemic, customers will likely expect a high degree of disinfection of products used on the bodies of humans, such as hair appliances.

In another embodiment, the professional stylist and cosmetologist will need to sterilize all their hair appliances and hair tool accessories like hair clips, combs, brushes, make up brushes, shears, phone and keys in between each client for state board and state regulations. Furthermore, during and after the time of the coronavirus pandemic, customers will likely expect a high degree of sterilization of products used on the bodies of humans, such as hair appliances.

The professional model unit comes with multiple push and go mounts that allows for the system to be mounted. These push and go mounts can get mounted in either a salon station, at home on the bathroom wall or anywhere else that a professional stylist chooses. The professional stylist kill be able to push a button that causes the release of the unit from being mounted on a wall or station. This flexibility further allows the professional to travel with the unit.

The professional model has a lid that secures the unit for travel, and has the UV sanitization and disinfection lights in the lid and front plate of the professional model. Also, the UV sanitization and disinfection lighting is located in the compartment containing the bottom half of the flat iron, curling iron and blow dryer, such that the UV sanitization and disinfection lighting sanitizes and disinfects the bottom half of the flat iron, curling iron and blow dryer.

The professional model, and retail model has a lid that secures the unit for travel, and has the UV-C sterilization lights in the lid for the professional, retail model. Also, the UV-C sterilization lighting is located in the compartment containing the bottom half of the flat iron, curling iron and blow dryer, such that the sterilization lighting sterilizes the bottom half of the flat iron, curling iron and blow dryer.

The professional model also allows the front plate to be removed and replaced for future add-ons and upgrades. The front plate is the same as the front cover or front plate of the system 116. The professional model has an option of a screen for a premium price, and that screen becomes the professional's store front to sell different beauty products to their clients.

In another embodiment of the invention meant to be used in a hotel room, the plugs to plug the appliances in for power, are on the inside of the unit. In contrast, in the embodiment of the invention that is the professional model, the power outlets are cleverly placed facing the outside of the unit so the customer ran plug and unplug the hair appliances at any time. This placement of the power outlets on the outside of the unit further allows the customer to replace the existing hair appliances with any other appliances that the customer chooses.

In contrast to the other embodiments of the invention, the Professional model does not come with appliances, as the professional will want to pick their own appliances.

In contrast to the other embodiments of the invention, the professional model auto shut off only turns the appliances off when the user shuts the lid of the unit.

The professional model does not have a cool down fan system. This allows the size of the unit to be smaller, thus saving money on material to enclose the unit, and thus bringing the cost of the unit down for the consumer. The reduced size and lack of a cool down fan system also reduces the weight of the unit, thus leading to increased portability.

In all models and embodiments of the present invention, ultraviolet UV-C light from the sanitization and disinfection and sterilization lights destroy multiple bacteria's and viruses. This is and will remain a serious concern because of the coronavirus pandemic. People will likely also be more concerned about germs, bacteria and viruses in general. The ultraviolet light from sanitization and disinfection and sterilization lights will disinfect and destroy all of these potential hazards, and thus prevent contamination to the customer, as well as ease the customer's mind about these concerns.

FIG. 1A

The Top view of the system 101 shows a view of the UV-C light equipped smart hair appliance organizer that is either wall mounted or a travel caddy system from the top.

The Front view of the system 102 shows a view of the UV-C light equipped smart hair appliance organizer that is either wall mounted or a travel caddy system from the front.

The Side view of the system 103 shows a view of the UV-C light equipped smart hair appliance organizer that is either wall mounted or a travel caddy system from the side.

Another Side view of the system 104 shows a view of the UV-C light equipped smart hair appliance organizer that is either wall mounted or a travel caddy system from the opposite side as The Side view of the system 103.

The Back view of the system 105 shows a view of the UV-C light equipped smart hair appliance organizer that is either wall mounted or a travel caddy system from the back.

The Bottom view of the system 106 shows a view of the UV-C light equipped smart hair appliance organizer that is either wall mounted or a travel caddy system from the bottom.

The Wire port for flat iron 107 is where the flat iron attaches to the UV-C light equipped smart hair appliance organizer that is either wall mounted or a travel caddy system.

The Wire port for curling iron 108 is where the curling iron attaches to the UV-C light equipped smart hair appliance organizer that is either wall mounted or a travel caddy system.

The Wire port for hair dryer 109 is where the hair dryer attaches to the UV-C light equipped smut hair appliance organizer that is either wall mounted or a travel caddy system.

The Reset button for the hair dryer 110 turns the hair dryer off and then on again.

The ON/OFF Button 111 toggles the system to turn on and start the sanitization and disinfection process by turning on ultraviolet lights. Or if the system is already on, then the button turns off the sanitization and disinfection system.

The Mounting location for hair dryer 112 is where the hair dryer is stored.

The Mounting location for curling iron 113 is where the curling iron is stored.

The Mounting location for flat iron 114 is where the flat iron is stored.

The Upper cover of the system 115 is a plate that covers the top of the UV equipped smart hair appliance organizer that is either wall mounted or a travel caddy system.

The front cover or front plate of the system 116 is removable by the user. The user can remove the front cover or front plate of the system 116 in case they want to purchase and install an upgraded front cover or front plate of the system 146. The upgraded version includes a screen and plays advertising on the screen. The advertising can be controlled from a remote location online. The screen also allows customers to buy hair appliances right from the screen, and the hair appliances will be shipped from a central shipping location or distribution center. This is an essential part of the business, because in addition to having a professional work on a customer's hair, customers sometimes want to work on their hair themselves, and for this they require hair appliances.

Furthermore, this way a customer can buy directly from a seller. This is in contrast to Amazon, which is well known for selling fake products, and non-authenticated products by sellers who are selling, products that are not actually manufactured by the companies that the seller claims they are manufactured by.

There is typically no other dynamic advertising in a hotel room, so a screen on the case of the invention in a hotel room might get a high degree of attention from a user, which might make the advertising on that screen very lucrative.

The Power cable 117 plugs into a power outlet to provide power for the system.

The Size cover of the system 118 is a plate that covers one side of the system.

The Hanging board of the system 119 is what allows the system to mount onto the wall.

The port for locker 120 accepts the locker 219. The system will eventually be mounted on the wall, and then the user may want to lock it. The user can optionally lock the system by placing the locker 219 into the port for locker 120. This will prevent anyone who is not the user from opening the system and taking the hair appliances or using the system.

FIG. 1B

Figure 1B:
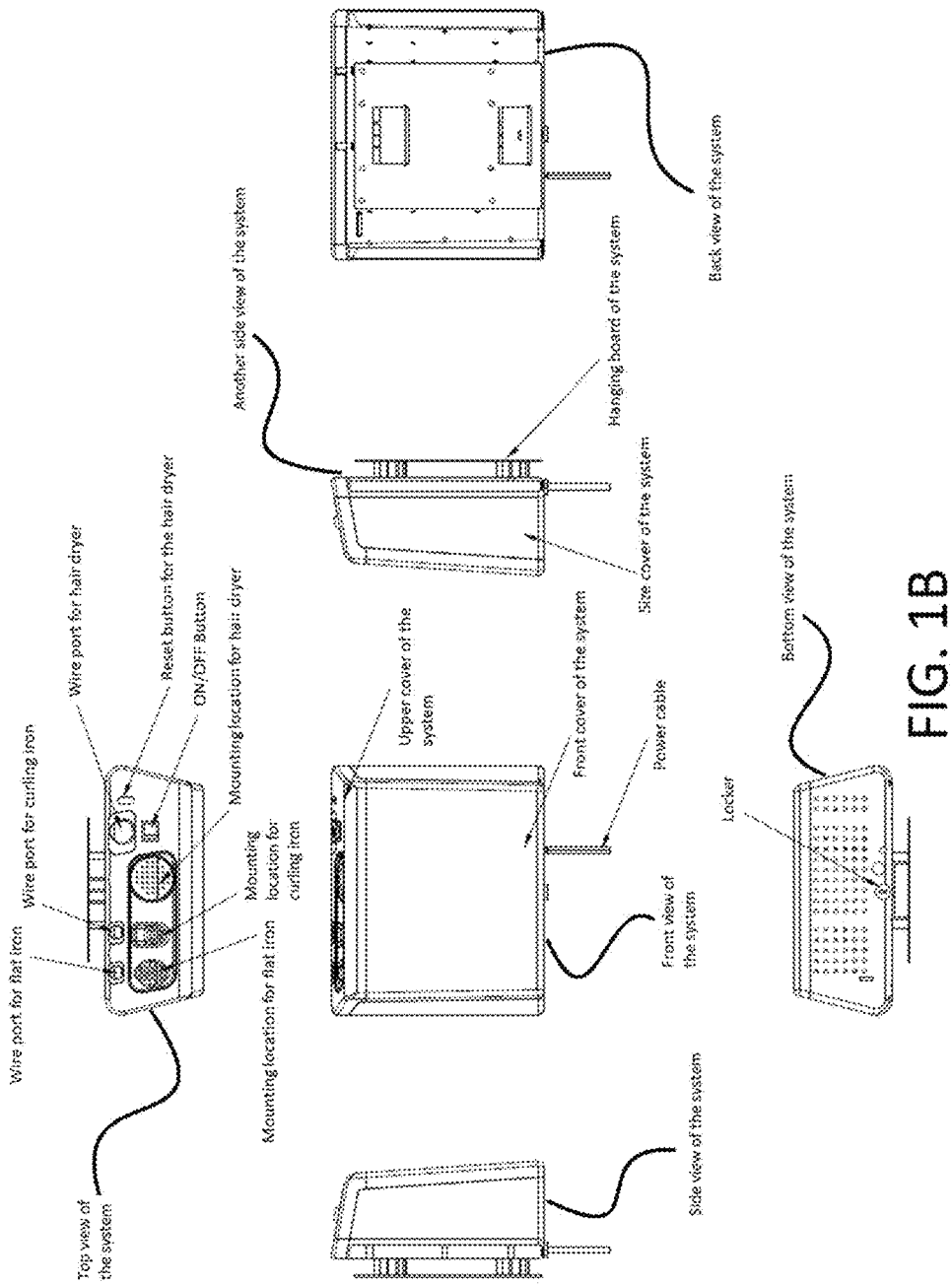
FIG. 1B is the schematic view of one embodiment of the UV-C light equipped smart hair appliance organizer that is either wall mounted or a travel caddy according to various embodiments of the present disclosure.

FIG. 1B is the same as FIG. 1A, except that instead of numbers as labels, the labels are phrases.

FIG. 2A

The Wire cover for the flat iron 201 covers the wire port for the flat iron 107 when the flat iron is not attached to the wire port for the flat iron 107.

The Wire cover for the curling iron 202 covers the wire port for the curling iron 108 when the curling iron is not attached to the wire port for the curling iron 108.

The Wire cover for the hair dryer 203 covers the wire port for the hair dryer 109 when the hair dryer is not attached to the wire port for the hair dryer 109.

The Upper cover of the system 204 is a plate that covers the top of the UV equipped smart hair appliance or that is either wall mounted or a travel caddy system.

The ON/OFF Button 205 toggles the system to turn on and start the sanitization and disinfection process by turning on ultraviolet lights. Or if the system is already on, then the button turns off the sanitization and disinfection system.

The Back cover of the system 206 is a plate that covers the back of the UV equipped smart hair appliance organizer that is either wall mounted or a travel caddy system.

Function control board of the light sanitizer and disinfecter 207

The Power cable 208 plugs into a power outlet to provide power for the system.

Power control board of the light sanitizer and disinfecter 209

The Power outlet cover 210 covers the power outlet.

The Remote control module 211 is able to accept incoming signals such that a future potential remote control can interact with the system by sending signals to the remote control module 211.

The Power outlets 212 are where the hair appliances can plug into to recharge.

The Front cover of the system 213 is the same as the front cover or front plate of the system 116.

The Hanging board of the system 214 is what allows the system to mount onto the wall.

The Wire cover of flat iron 215 covers the wire port for the flat iron 107 when the flat iron is not attached to the wire port for the flat iron 107.

The Wire cover of curling iron 216 covers the wire port for the curling iron 108 when the curling iron is not attached to the wire port for the curling iron 108.

The Wire cover of hair dryer 217 covers the wire port for the hair dryer 109 when the hair dryer is not attached to the wire port for the hair dryer 109.

The Lower fastening cover of light sanitizer and disinfecter 218 can in one embodiment of the invention be a board that holds the sanitization and disinfection lights 223. In another embodiment of the invention, the lower fastening cover of light sanitizer and disinfecter 218 can be multiple boards that hold sanitization and disinfection lights. In another embodiment of the invention, the lower fastening cover of light sanitizer and disinfecter 218 can be a long board, as in longer than a normal sized board. In another embodiment of the invention, the lower fastening cover of light sanitizer and disinfecter 218 can be multiple long boards.

Locker 219 can be optionally used to lock the system by placing the locker 219 into the port for locker 120. This will prevent anyone who is not the user from opening the system and taking the hair appliances or using the system.

The Upper fastening cover of light sanitizer and disinfecter 220 can in one embodiment of the invention be a board that holds the sanitization and disinfection lights 223. In another embodiment of the invention, the upper fastening cover of light sanitizer and disinfecter 220 can be multiple boards that hold sanitization and disinfection lights. In another embodiment of the invention, the upper fastening, cover of light sanitizer and disinfecter 220 can be a long board, as in longer than a normal sized board. In another embodiment of the invention, the upper fastening cover of light sanitizer and disinfecter can be multiple long boards.

The Fan cover 221 covers the Cooling air fan 222.

The Cooling air fan 222 is close to the hair appliances so that the cooling air fan 222 can cool down the hair appliances more efficiently, as well as cool down the sanitization and disinfection lights 223.

Regarding the sanitization and disinfection lights 223, each Lower fastening cover of light sanitizer and disinfecter 218 includes multiple sanitization and disinfection lights, and the user could easily mount each board of sanitization and disinfection lights into the appropriate slot of the Lower fastening cover of light sanitizer and disinfecter 218. In one embodiment of the invention, each Lower fastening cover of light sanitizer and disinfecter 218 is a long board with multiple sanitization and disinfecter lights 223. In another embodiment of the invention, there are multiple Lower fastening cover of light sanitizer and disinfecter 218, each one being a board, and each board having multiple sanitization and disinfection lights 223 placed in the appropriate slot of each board.

The sanitization and disinfection lights 223 fill up all available space on each Lower fastening cover of light sanitizer and disinfecter 218.

In one embodiment of the invention, each long board with sanitization and disinfection lights 223 can be mounted into the slot of Lower fastening cover of light sanitizer and disinfecter 218.

Multiple boards can be useful and necessary because when each hair appliance has a board on each side, and each board has sanitization and disinfection lights pointed at the hair appliance, then more of the hair appliance can be disinfected and sanitized, because more surface area will be covered and so more germs and viruses will be destroyed.

Regarding the sanitization and disinfection lights 223, each Upper fastening cover of light sanitizer and disinfecter 220 includes multiple sanitization and disinfection lights, and the user could easily mount each board of sanitization and disinfection lights into the appropriate slot of the Upper fastening cover of light sanitizer and disinfecter 220. In one embodiment of the invention, each Upper fastening cover of light sanitizer and disinfecter 220 is a long board with multiple sanitization and disinfection lights 223. In another embodiment of the invention, there are multiple Upper fastening cover of light sanitizer and disinfecter 220, each one being a board, and each board having multiple sanitization and disinfection lights 223 placed in the appropriate slot of each board.

The sanitization and disinfection lights 223 fill up all available space on each Upper fastening cover of light sanitizer and disinfecter 220.

In one embodiment of the invention, each long board with sanitization and disinfection lights 223 can be mounted into the slot of Upper fastening cover of light sanitizer and disinfecter 220.

FIG. 2B

Figure 2A:
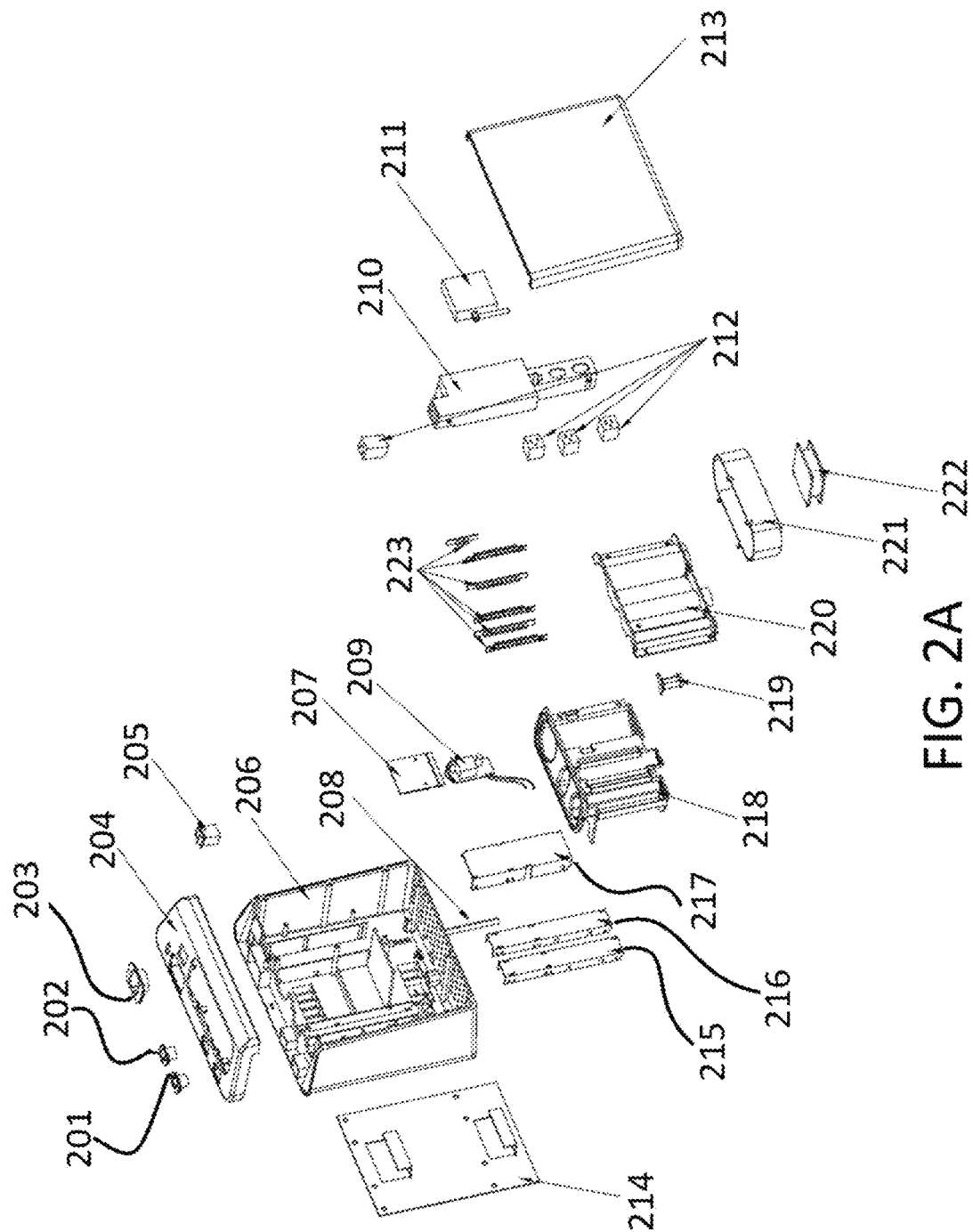
FIG. 2A is the schematic view of another embodiment of the UV-C light equipped smart hair appliance organizer that is either wall mounted or a travel caddy according to various embodiments of the present disclosure.
Figure 2B:
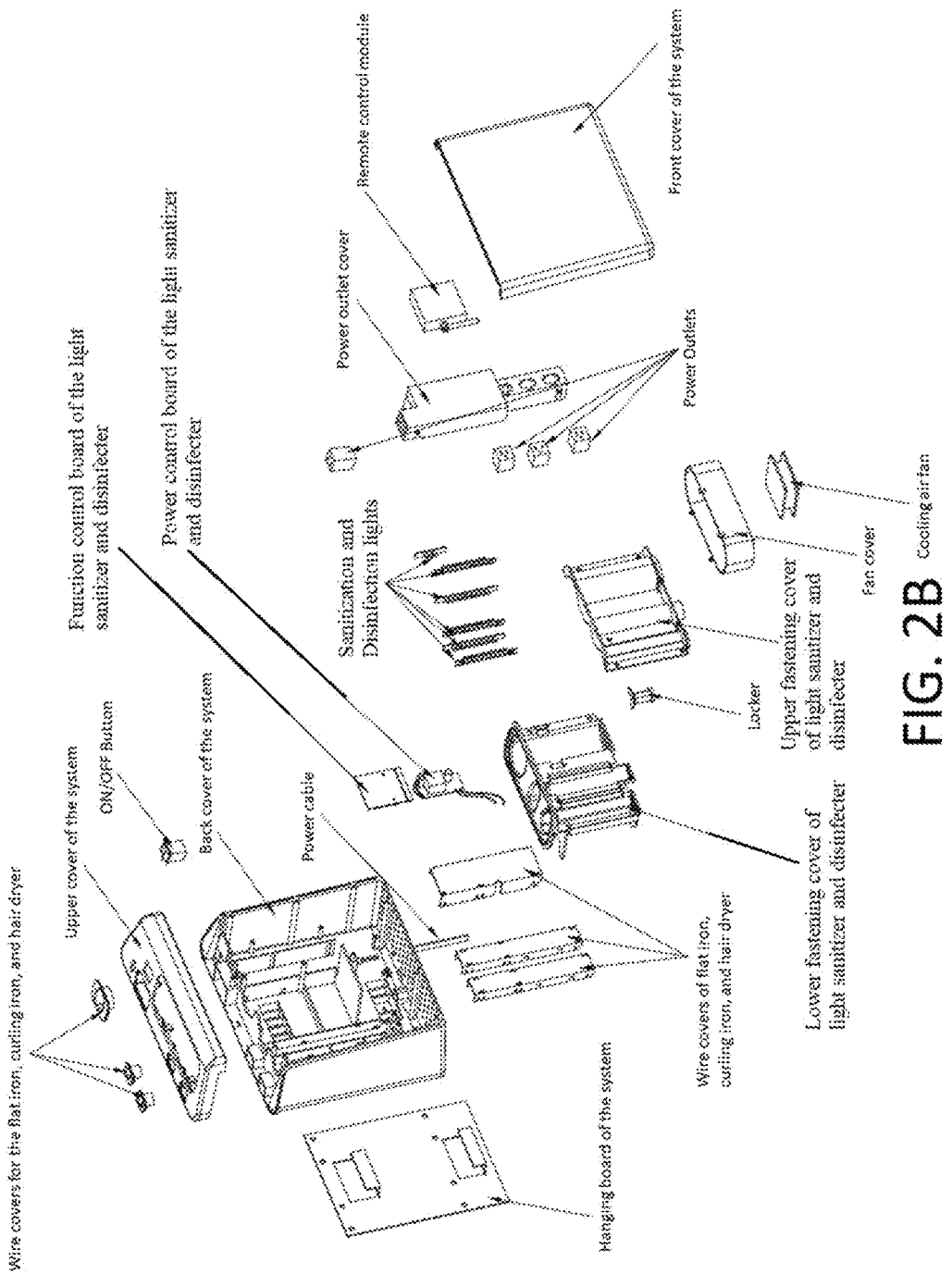
FIG. 2B is the schematic view of another embodiment of the UV-C light equipped smart hair appliance organizer that is either wall mounted or a travel caddy according to various embodiments of the present disclosure.

FIG. 2B is the same as FIG. 2A, except that instead of numbers as labels, the labels are phrases.

FIG. 3A

The cooling air fan 301 is close to the hair appliances so that the cooling air fan 301 can cool down the hair appliances more efficiently. That is, since the cooling air fan 301 is close to the hair appliances, less cooling effect is wasted.

Cable showing how to connect the hair dryer to the power outlet inside the system 302. The cable is coded so that it is easier to organize as opposed to a non-coiled cable.

Cable showing how to connect the light sanitizer and disinfecter to the PC board inside the system 303. The cable is coiled so that it is easier to organize as opposed to a non-coiled cable.

Cable showing how to connect the curling iron to the power outlet inside the system 304. The cable is coiled so that it is easier to organize as opposed to a non-coiled cable.

Cable showing how to connect the flat iron to the power outlet inside the system 305. The cable is coiled so that it is easier to organize as opposed to a non-coiled cable.

FIG. 3B

Figure 3A:
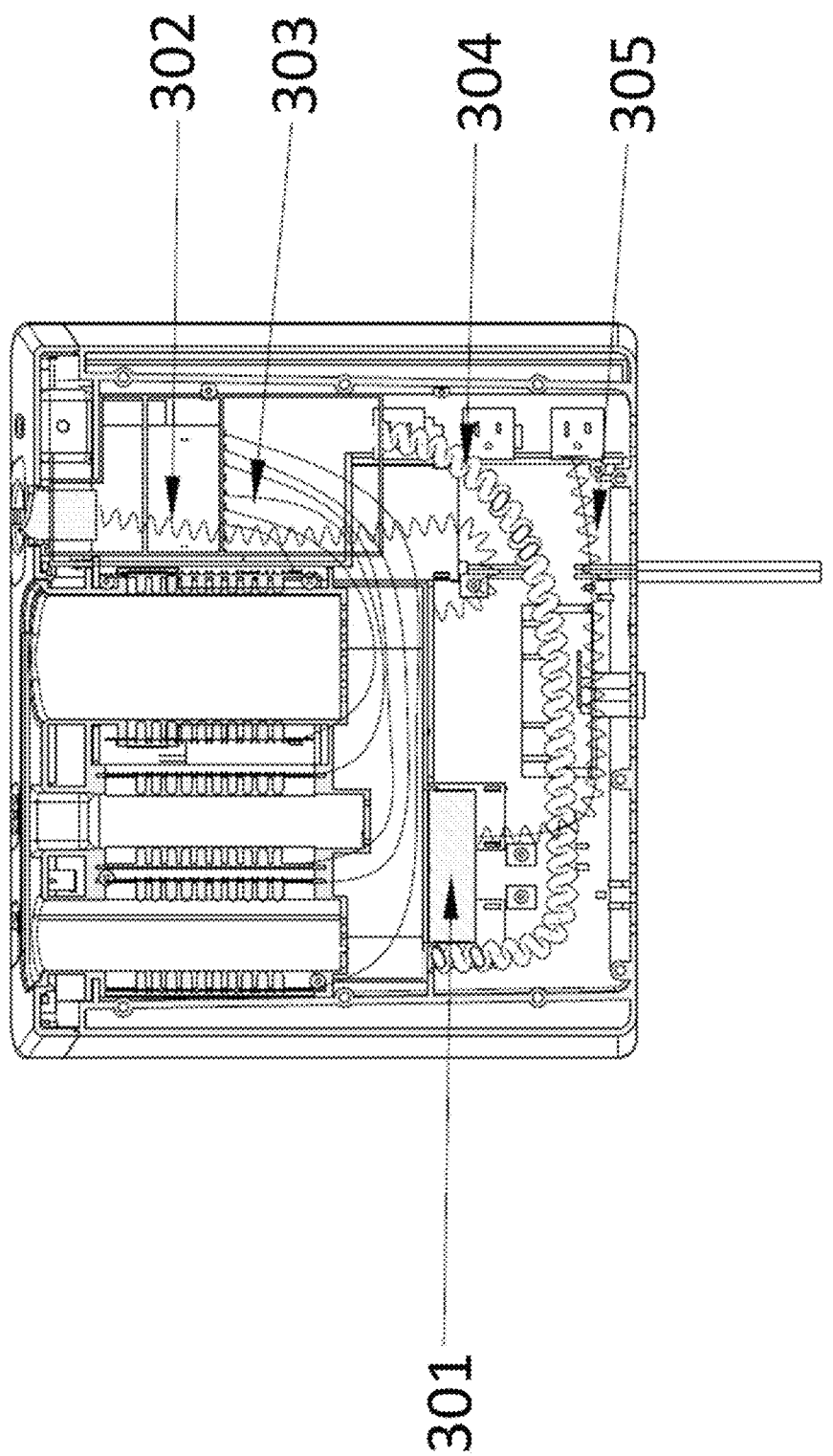
FIG. 3A is the schematic view of the third embodiment of the UV-C light equipped smart hair appliance organizer that is either wall mounted or a travel caddy according to various embodiments of the present disclosure.
Figure 3B:
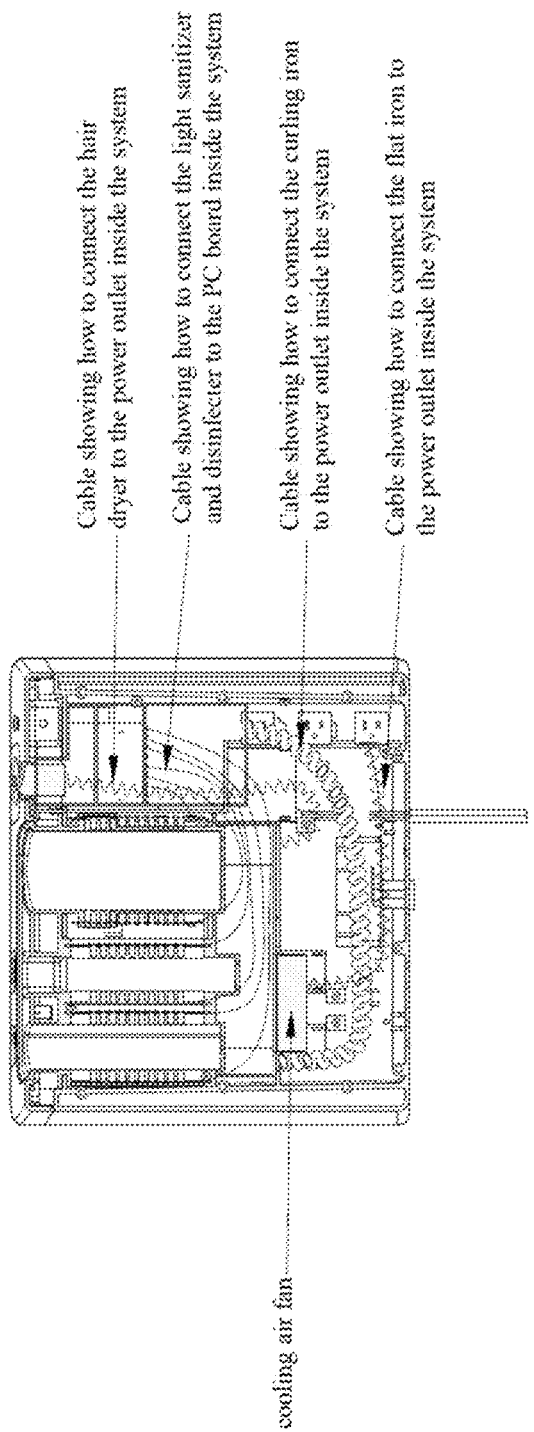
FIG. 3B is the schematic view of the third embodiment of the UV-C light equipped smart hair appliance organizer that is either wall mounted or a travel caddy according to various embodiments of the present disclosure.

FIG. 3B is the same as FIG. 3A, except that instead of numbers as labels, the labels are phrases.

Figure 4:
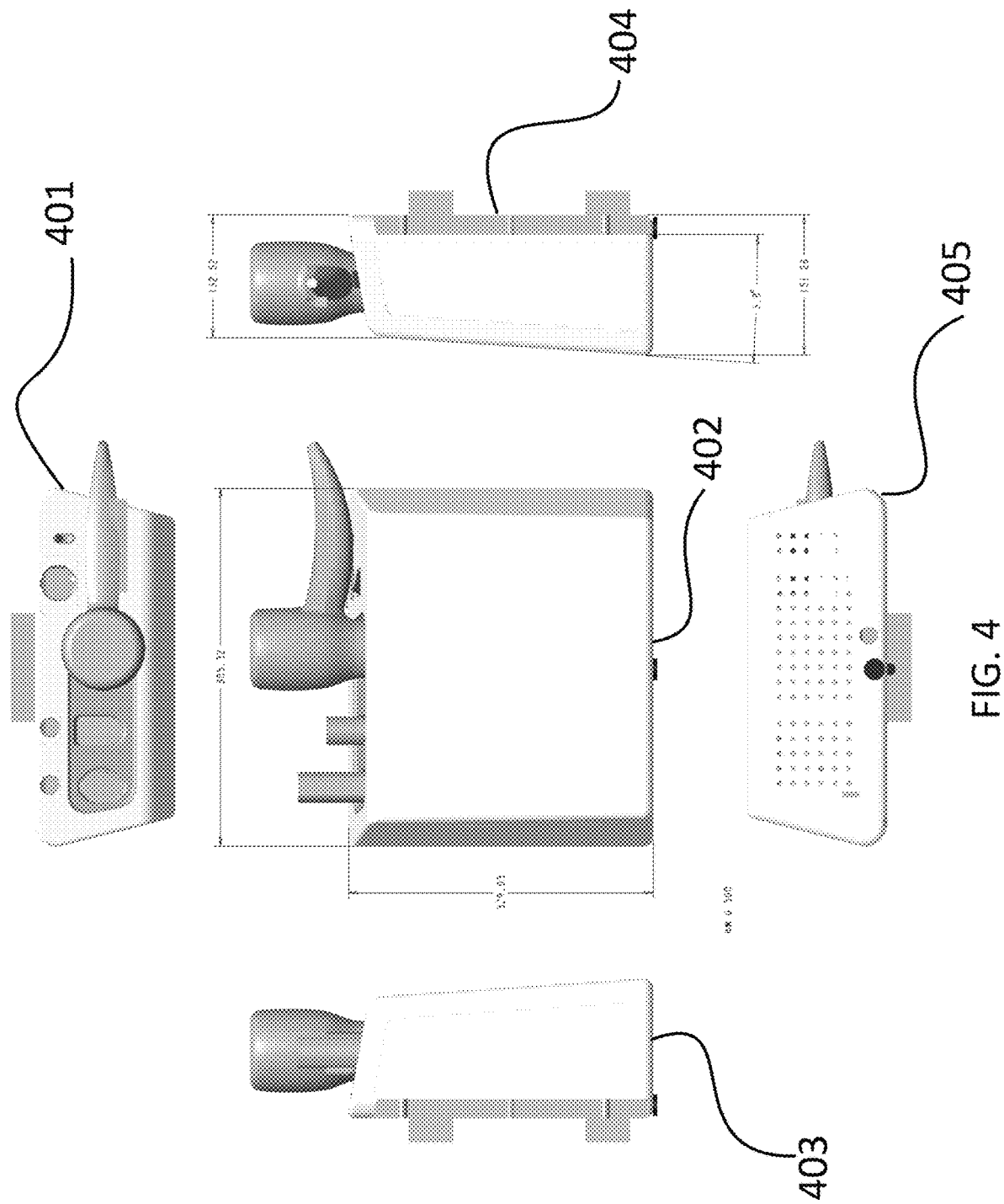
FIG. 4 shows different views of the system with the hair appliances of flat iron, curling iron, and hair dryer in place according to various embodiments of the present disclosure.

FIG. 4 shows different views of the system with the hair appliances of flat iron, curling iron, and hair dryer in place. There is no size restriction on the hair appliances, however, the wire port of each hair appliance must fit into the designated wire port in the system. For example, a wire port on a flat iron, must fit the Wire port for flat iron 107. Similarly the wire port for a curling iron must fir the Wire port for curling iron 108 and the wire port for a hair dryer must fit the Wire port for hair dryer 109.

The Top view of the system 401 shows a view of the UV-C light equipped smart hair appliance organizer that is either wall mounted or a travel caddy system from the top, with a hair appliance attached.

The Front view of the system 402 shows a view of the UV-C light equipped smart hair appliance organizer that is either wall mounted or a travel caddy system from the front, with a hair appliance attached.

The Side view of the system 403 shows a view of the UV-C light equipped smart hair appliance organizer that is either wall mounted or a travel caddy system from the side, with a hair appliance attached.

Another Side view of the system 404 shows a view of the UV-C light equipped smart hair appliance organizer that is either wall mounted or a travel caddy system from the opposite side of the Side view of the system 403, with a hair appliance attached.

The Bottom view of the system 405 shows a view of the UV-C light equipped smart hair appliance organizer that is either wall mounted or a travel caddy system from the bottom, with a hair appliance attached.

Figure 5:
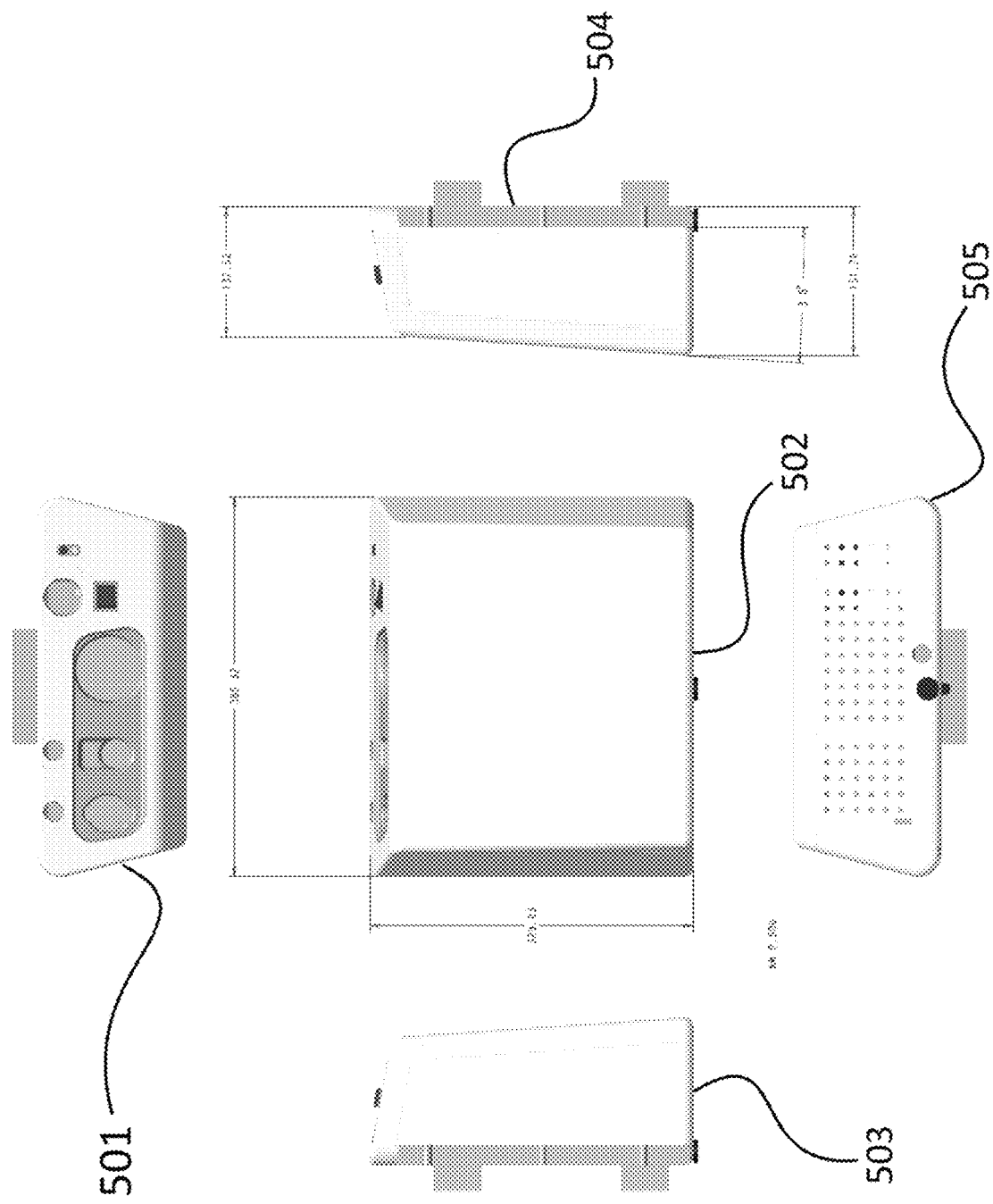
FIG. 5 shows different views of the system alone without the hair appliances according to various embodiments of the present disclosure.

FIG. 5 shows different views of the system without the hair appliances attached.

The Top view of the system 501 shows a view of the UV-C light equipped smart hair appliance organizer that is either wall mounted or a travel caddy system from the top, without a hair appliance attached.

The Front view of the system 502 shows a view of the UV-C light equipped smart hair appliance organizer that is either wall mounted or a travel caddy system from the front, without a hair appliance attached.

The Side view of the system 503 shows a view of the UV-C light equipped smart hair appliance organizer that is either wall mounted or a travel caddy system from the side, without a hair appliance attached.

Another Side view of the system 504 shows a view of the UV-C light equipped smart hair appliance organizer that is either wall mounted or a travel caddy system from the opposite side as the Side view of the system 503, without a hair appliance attached.

The Back view of the system 505 shows a view of the UV-C light equipped smart hair appliance organizer that is either wall mounted or a travel caddy system from the back, without a hair appliance attached.

The Bottom view of the system 506 shows a view of the UV-C light equipped smart hair appliance organizer that is either wall mounted or a travel caddy system from the bottom, without a hair appliance attached.

FIG. 6

Figure 6:
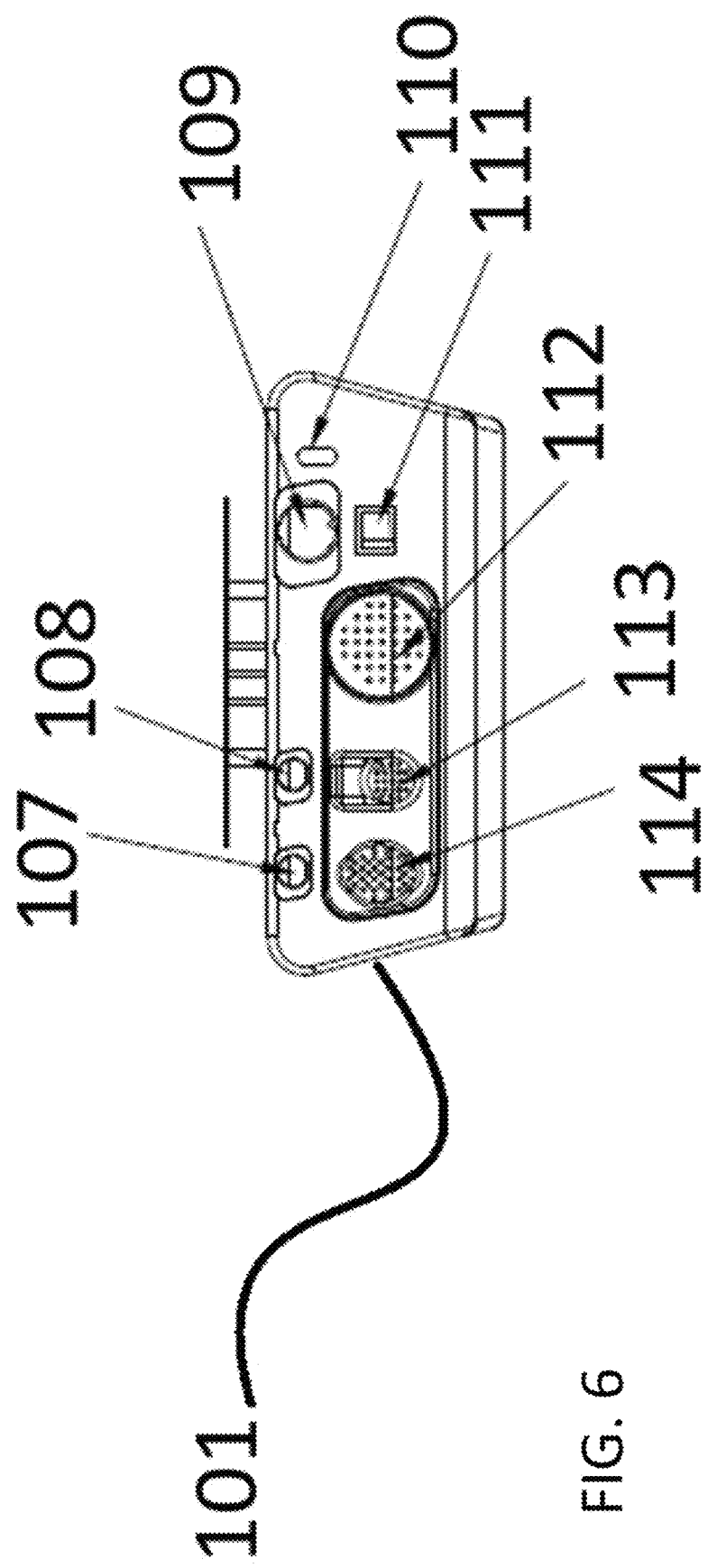
FIG. 6 shows a zoomed in version of certain parts of the invention according to various embodiments of the present disclosure.

FIG. 6 is the zoomed in version of parts 101 anti 107-114 from FIG. 1A. This provides a more detailed view of these parts.

FIG. 7

Figure 7:
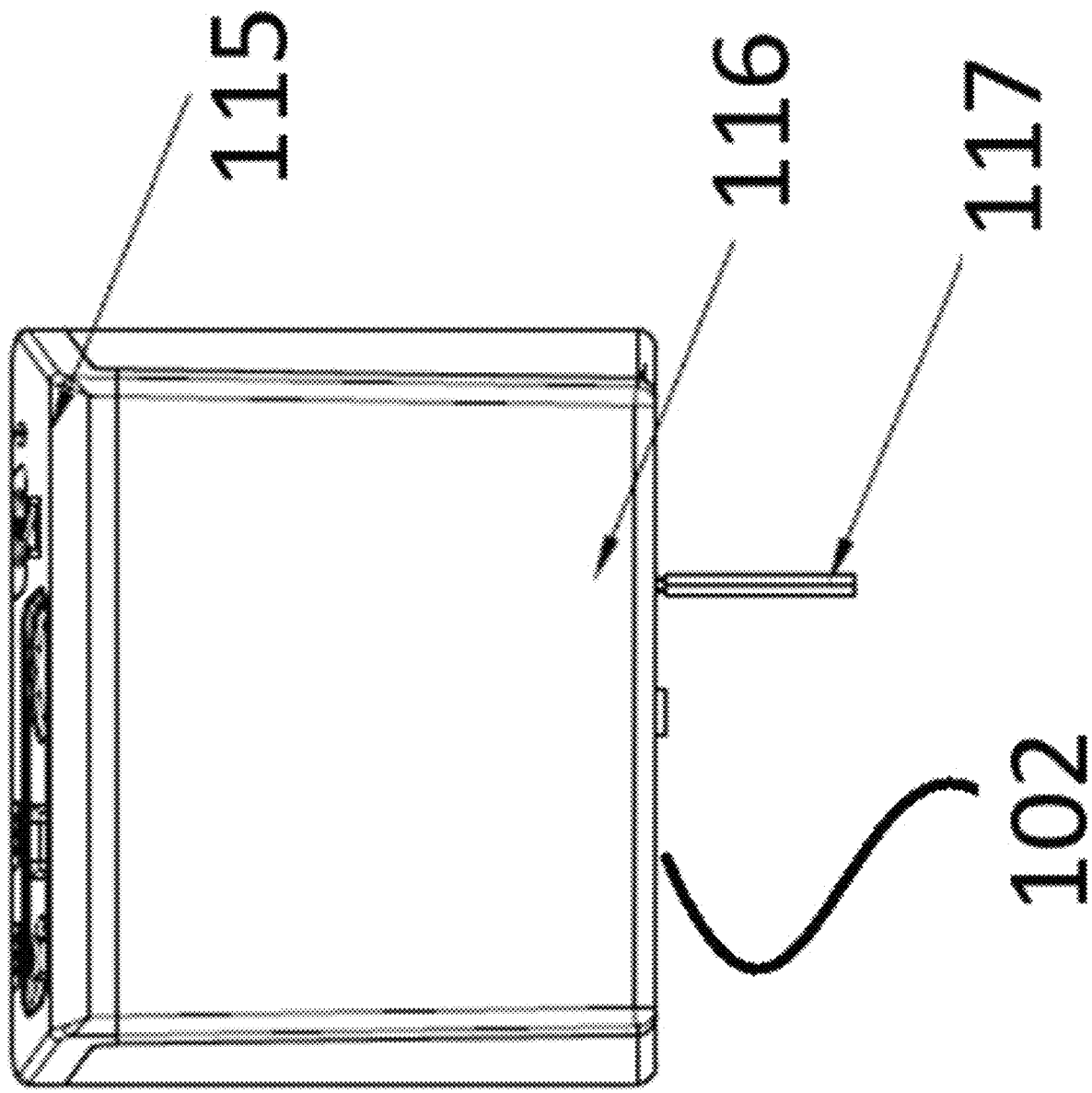
FIG. 7 shows a zoomed in version of certain parts of the invention according to various embodiments of the present disclosure.

FIG. 7 is the zoomed in version of parts 102 and 115-117 from FIG. 1A. This provides a more detailed view of these parts.

FIG. 8

Figure 8:
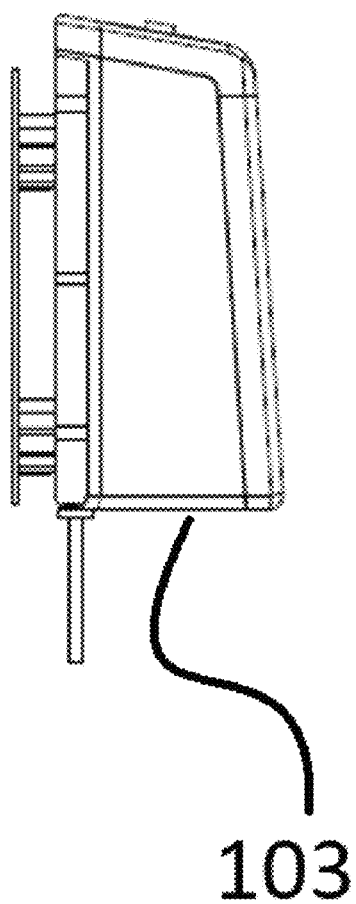
FIG. 8 shows a zoomed in version of certain parts of the invention according to various embodiments of the present disclosure.

FIG. 8 is the zoomed in version of part 103 from FIG. 1A. This provides a more detailed view of this part.

FIG. 9

Figure 9:
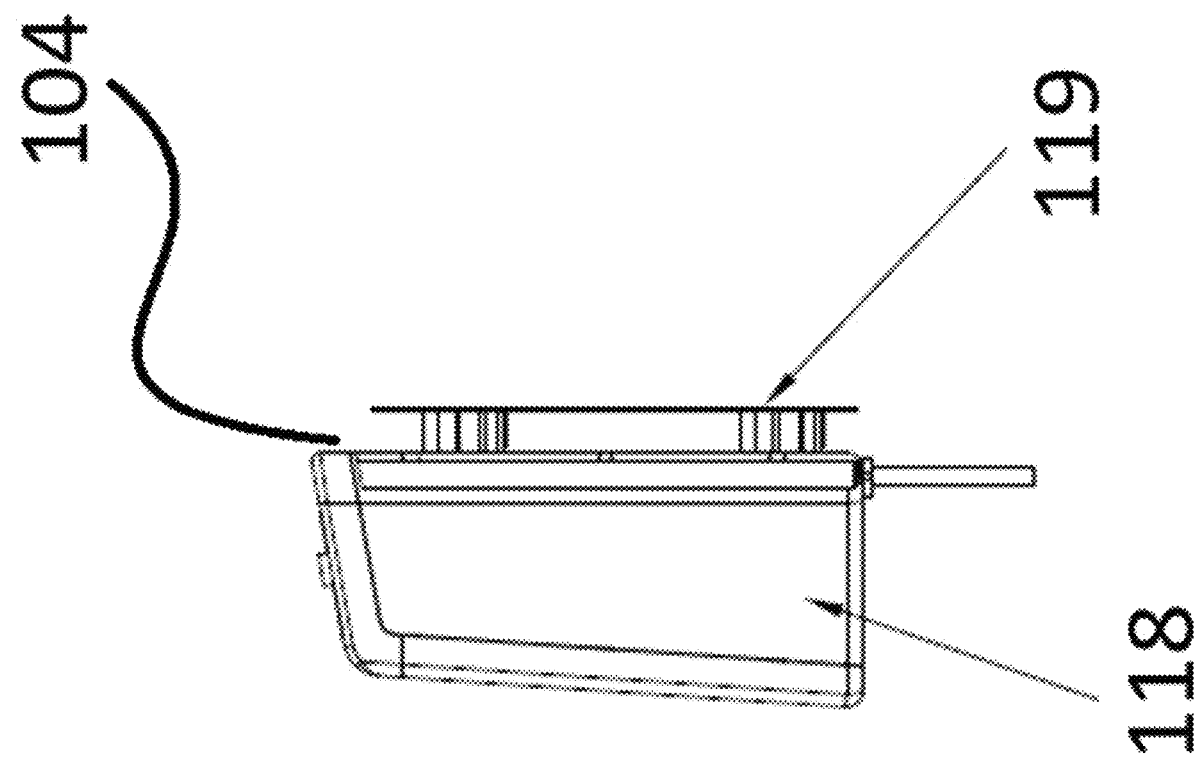
FIG. 9 shows a zoomed in version of certain parts of the invention according to various embodiments of the present disclosure.

FIG. 9 is the zoomed in version of parts 104 and 118-119 from FIG. 1A. This provides a more deralied view of these parts.

FIG. 10

Figure 10:
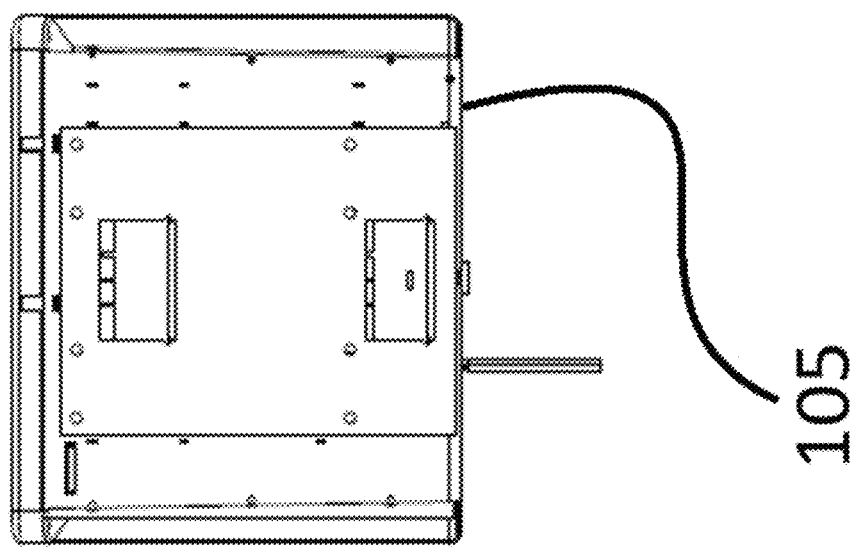
FIG. 10 shows a zoomed in version of certain parts of the invention according to various embodiments of the present disclosure.

FIG. 10 is the zoomed in version of part 105 from FIG. 1A. This provides a more detailed view of this part.

FIG. 11

Figure 11:
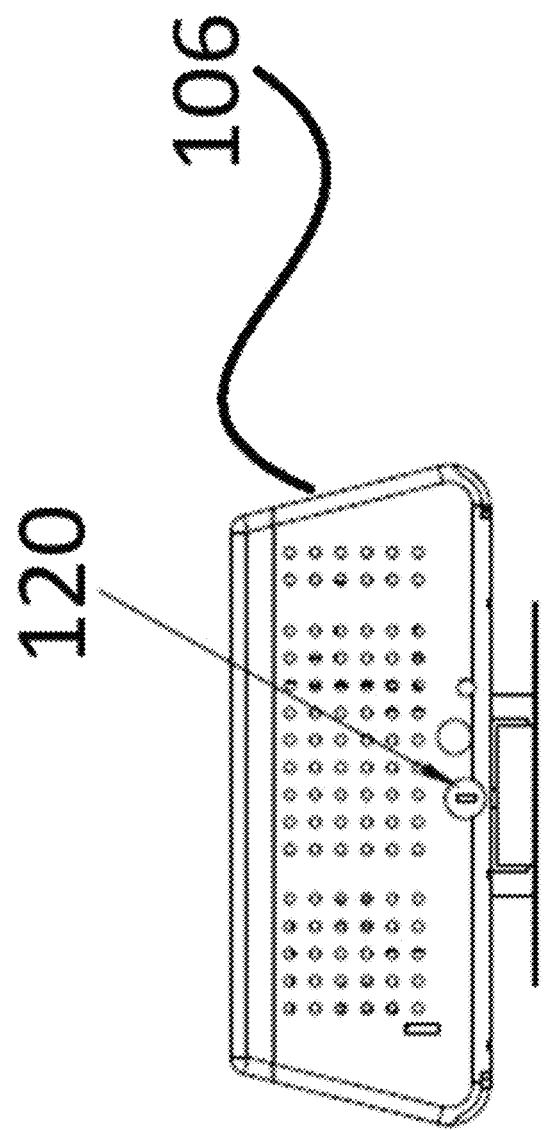
FIG. 11 shows a zoomed in version of certain parts of the invention according to various embodiments of the present disclosure.

FIG. 11 is the zoomed in version of parts 106 and 120 from FIG. 1A. This provides a more detailed view of these parts.

FIG. 12

Figure 12:
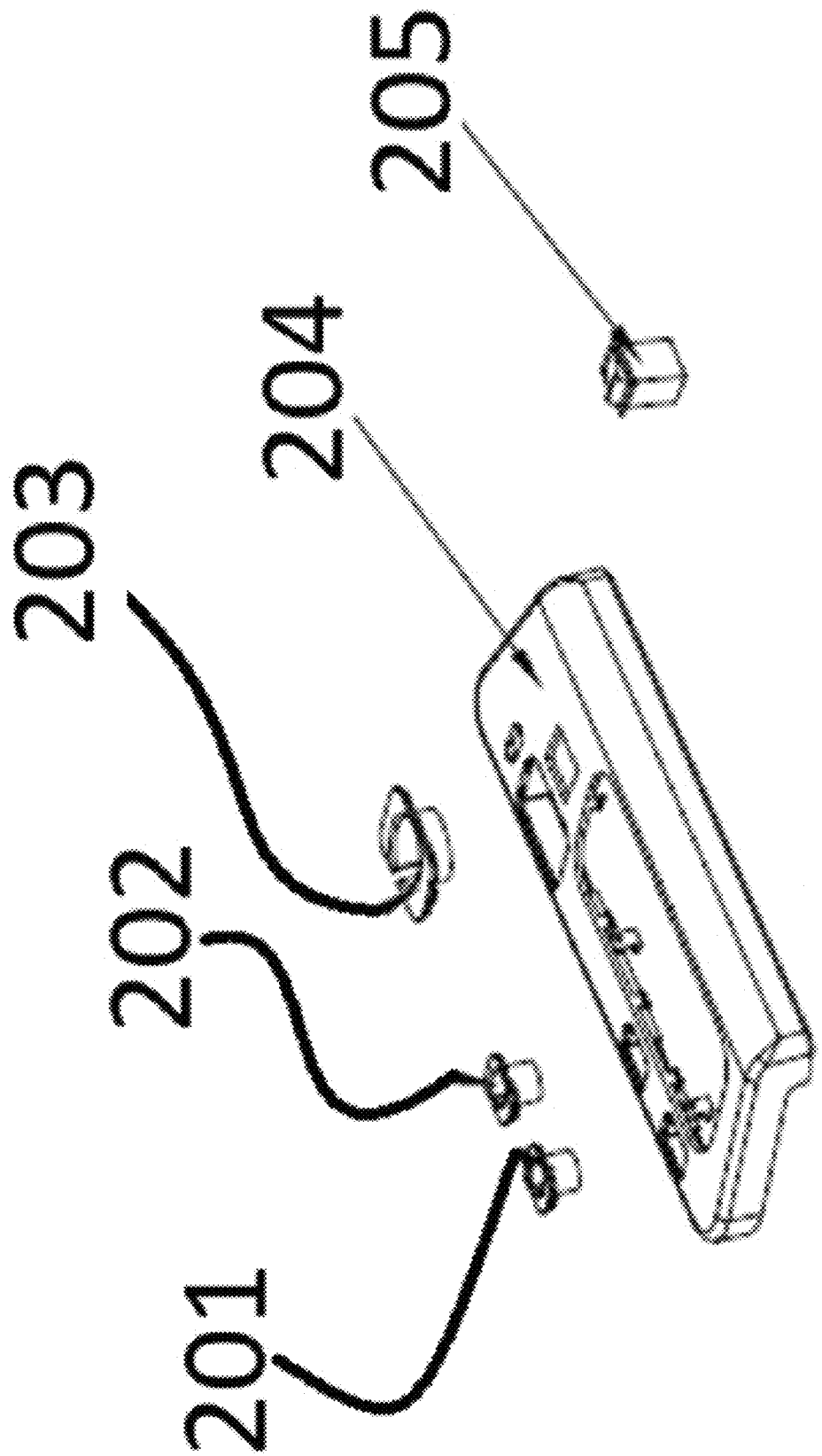
FIG. 12 shows a zoomed in version of certain parts of the invention according to various embodiments of the present disclosure.

FIG. 12 is the zoomed in version of parts 201-205 from FIG. 2A. This provides a more detailed view of these parts.

FIG. 13

Figure 13:
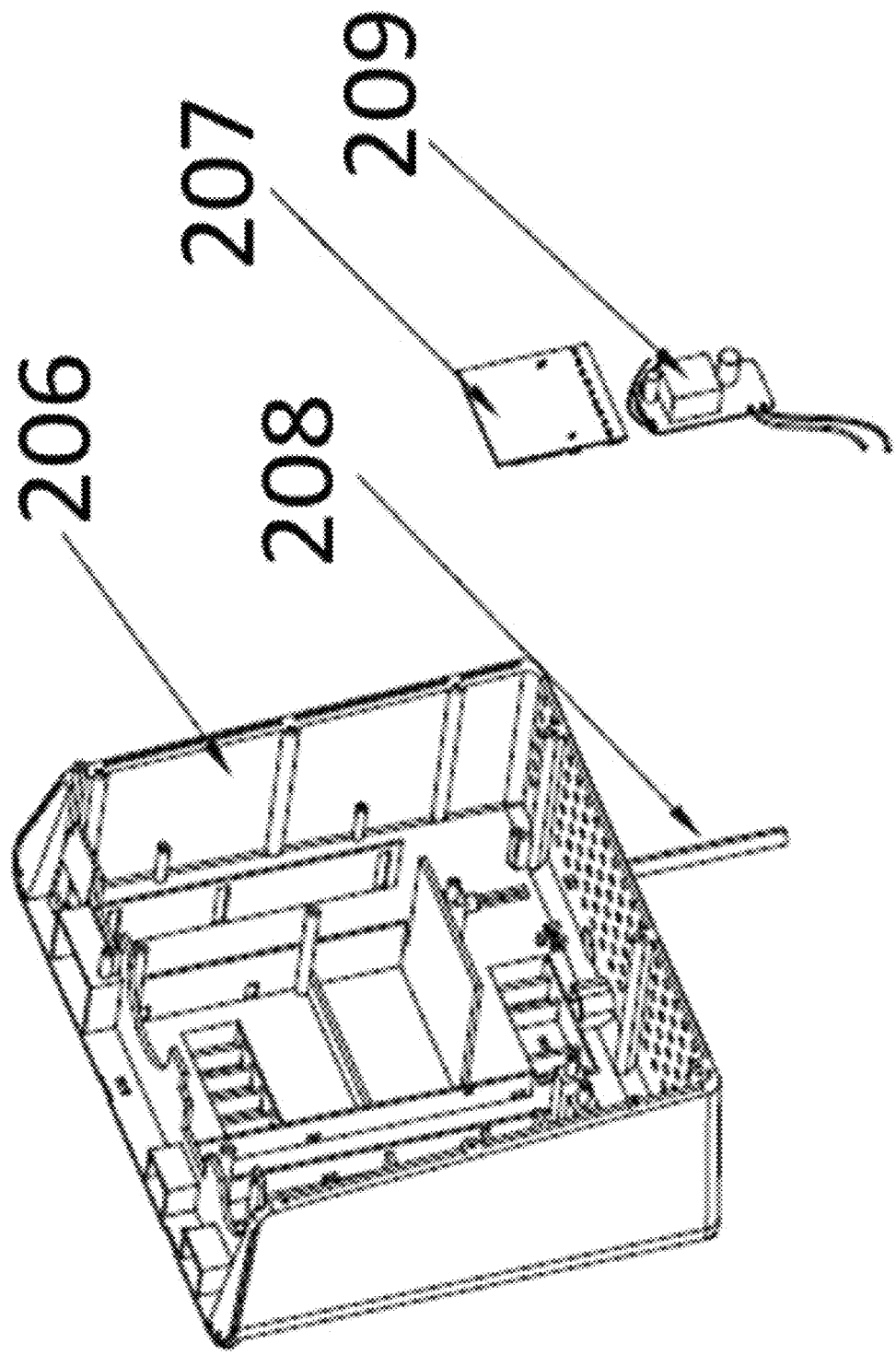
FIG. 13 shows a zoomed in version of certain parts of the invention according to various embodiments of the present disclosure.

FIG. 13 is the zoomed in version of parts 206-209 from FIG. 2A. This provides a more detailed view of these parts.

FIG. 14

Figure 14:
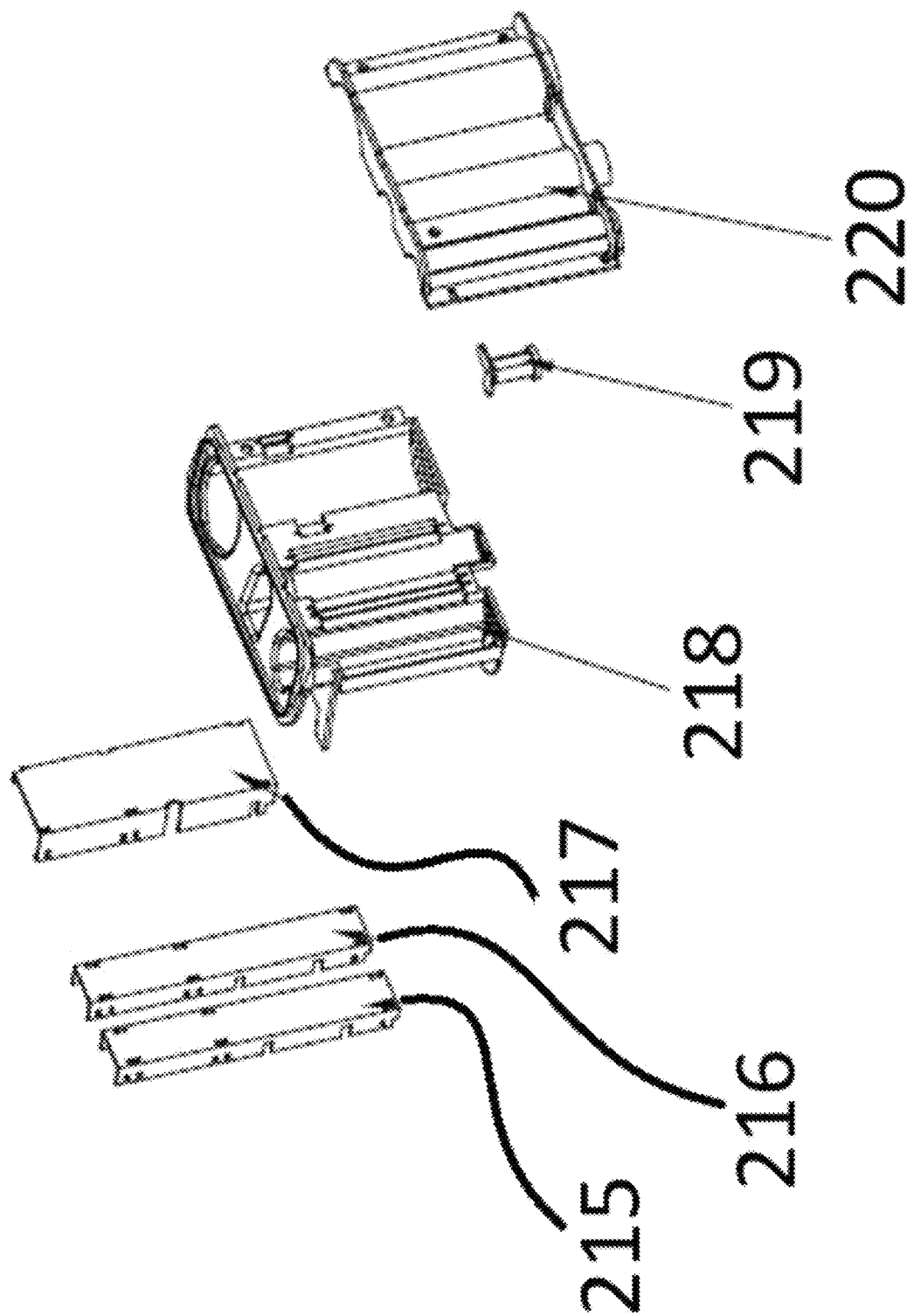
FIG. 14 shows a zoomed in version of certain parts of the invention according to various embodiments of the present disclosure.

FIG. 14 is the zoomed in version of parts 215-220 from FIG. 2A. This provides a more detailed view of these parts.

FIG. 15

Figure 15:
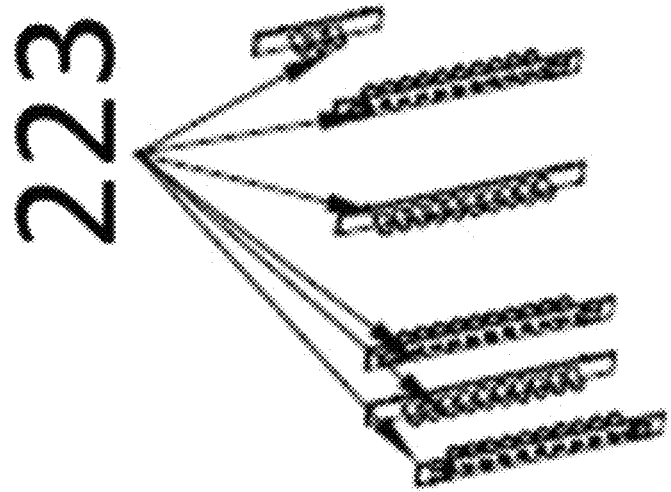
FIG. 15 shows a zoomed in version of certain parts of the invention according to various embodiments of the present disclosure.

FIG. 15 is the zoomed in version of part 223 from FIG. 2A. This provides a more detailed view of this part.

Figure 16:
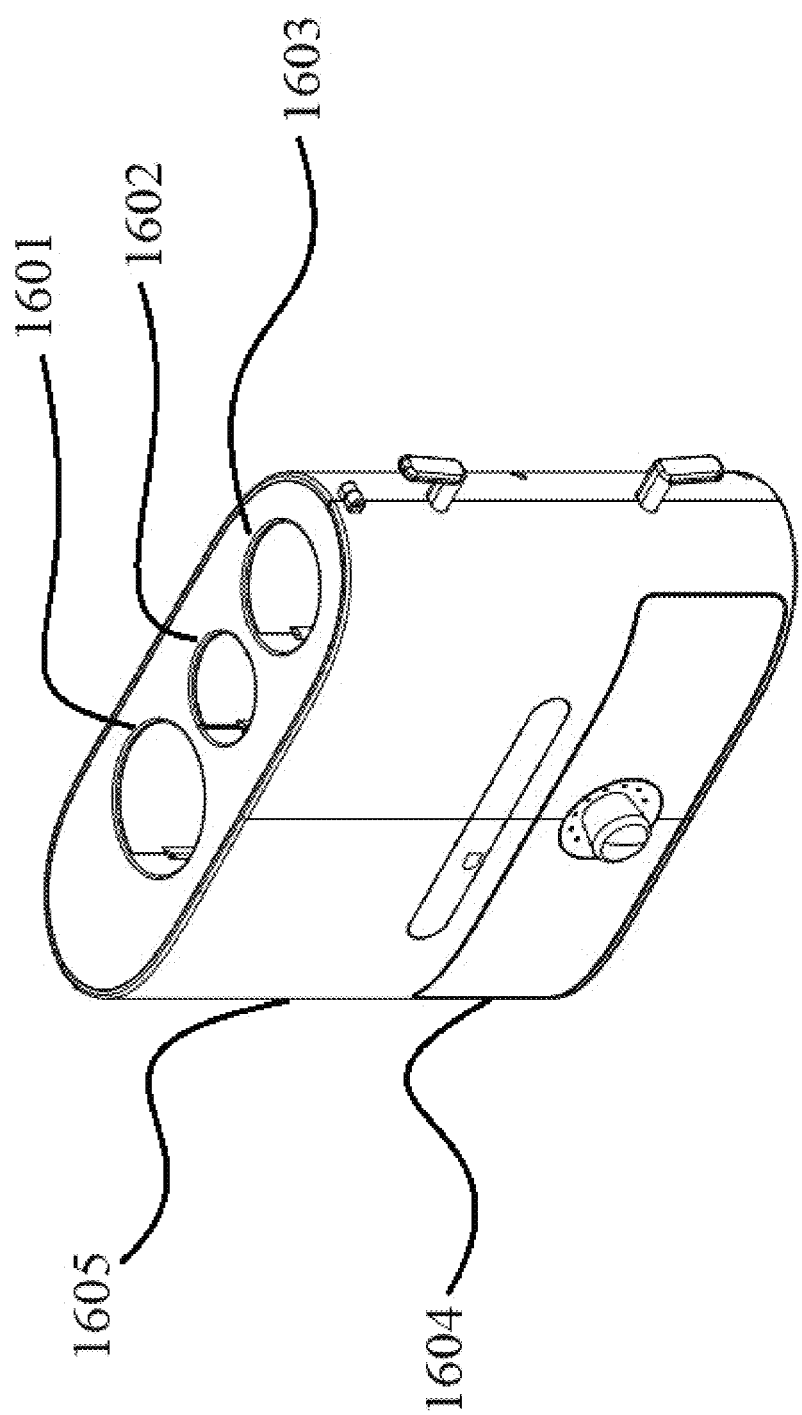
FIG. 16 is the view of one embodiment of the UV-C light equipped smart hair appliance organizer that is either wall mounted or a travel caddy according to various embodiments of the present disclosure.

FIG. 16 shows another embodiment of the organizer 1605. There are 3 holes 1601, 1602, and 1603 on the top of the organizer, allowing for hair appliances to be put in. These hair appliances could be a hair dryer, curling iron and flat iron. The size of each hole is designed for the front part of the hair appliances to be put into the hole.

Inside each hole on each side of the hole are ultraviolet lights producing a dual wave of ultraviolet light, both UVA and UVC, that disinfects and sterilizes the exposed part of the hair appliances. There is also a drawer 1604 that can be palled open, wherein additional hair appliances can be placed. When closed and items detected in the drawer, ultraviolet lights in the drawer produce a dual wave of ultraviolet light, both UVA and UVC, that disinfects and sterilizes the hair appliances inside the drawer.

The sterilization timing can be preset, and can vary from between 20 seconds to 3 minutes. Different embodiments can have different UVA bandwidths and different UVC bandwidths. The size of the holes can also vary in different embodiments, in case different hair appliances are used and need to be disinfected and sterilized.

Figure 17:
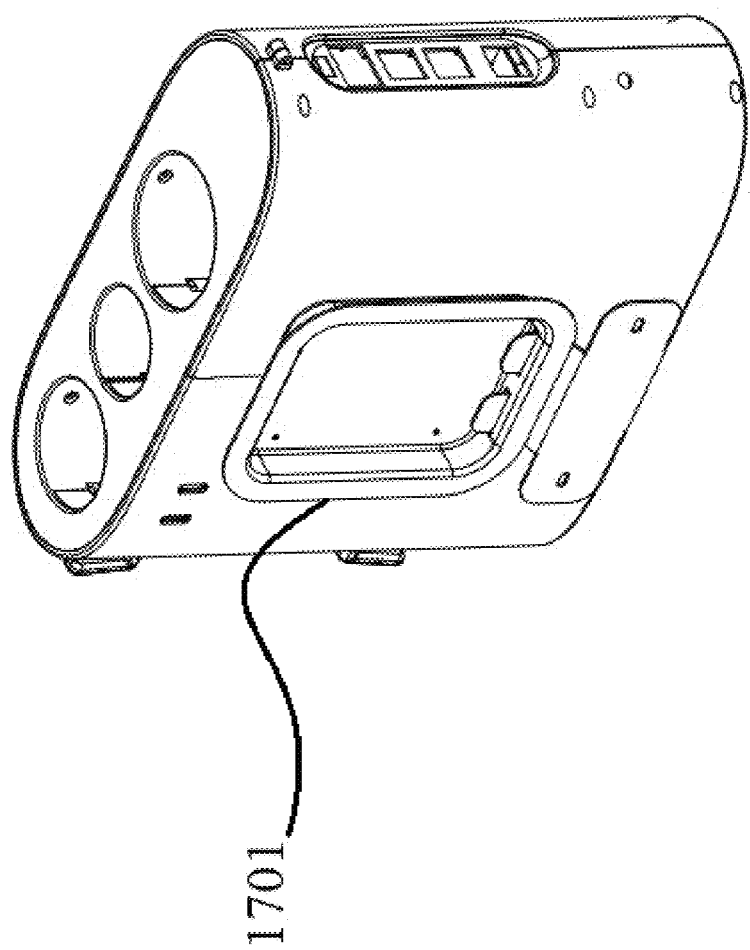
FIG. 17 is the view of one embodiment of the UV-C light equipped smart hair appliance organizer that is either wall mounted or a travel caddy according to various embodiments of the present disclosure.
Figure 18:
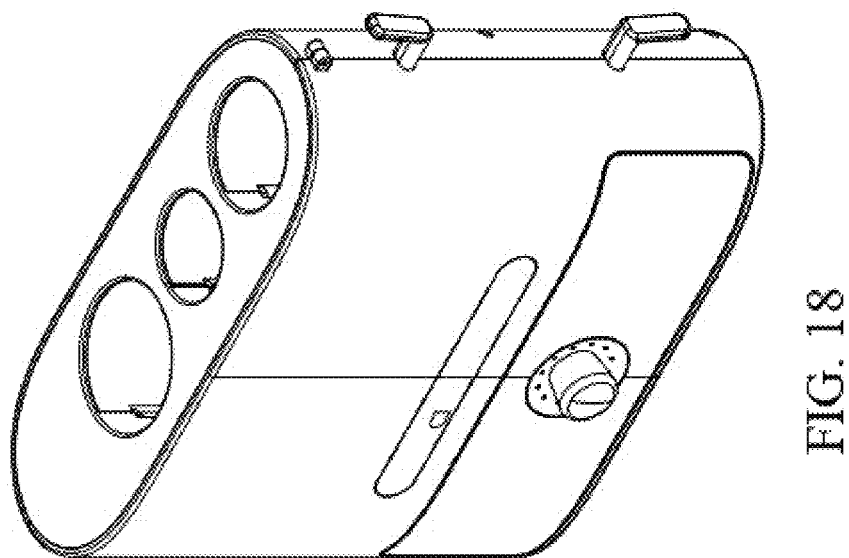
FIG. 18 is the same embodiment and view of the organizer as FIG. 16, except it shows the organizer with no explanatory lines.

FIG. 17 is the same embodiment of the organizer as FIG. 16, but instead shows the opposite side of the organizer. There is a semi rectangular device 1701 that can be used to mount the organizer onto a wall. This can be done by fitting the semi-rectangular device 1701 onto a device mounted onto the wall, such that the organizer is stable on the wall. The organizer could optionally then be more permanently attached to the wall using push mounts or screws, FIG. 18 is the same embodiment and view of the organizer as FIG. 16, except it shows the organizer with no explanatory lines.

Figure 19:
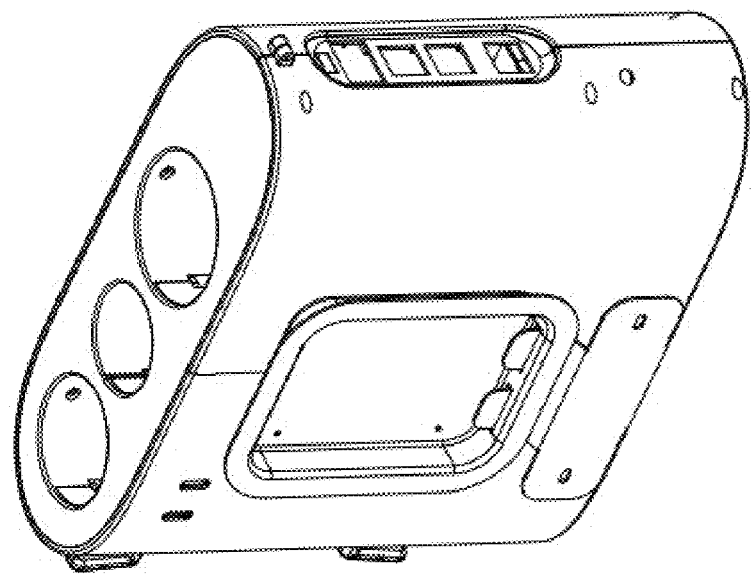
FIG. 19 is the same embodiment and view of the organizer as FIG. 17, except it shows the organizer with no explanatory lines.

FIG. 19 is the same embodiment and view of the organizer as FIG. 17, except it shows the organizer with no explanatory lines.

In another embodiment of the present invention, there is a system for a UV equipped smart hair appliance organizer that can be mounted on a wall with multiple push and go mounts, or taken off the wall and closed with a lid for portability; the lid containing sanitization and disinfection lights that shine ultraviolet light on hair appliances; power outlets on the outside of the system; coiled cords connecting the hair appliances to the system; a front plate on the system that is removable such that the front plate can be replaced with another front plate containing a display screen for the purpose of advertisements; a memory coupled to a processor, the memory comprising a plurality of instructions that cause the processor to: utilize lasers in order to detect the presence of hair appliances within the wall mounted system; automatically shut off the hair appliances after a preset time period of the hair appliances being inside the system; automatically turn on ultraviolet lights for the purpose of sanitization and disinfection of the hair appliances inside the system as soon as the wall mounted system is closed; automatically shut off the ultraviolet lights after a preset time period; utilize a cooling down system in order to prevent the ultraviolet lights from overheating and in order to prevent the hair appliances from overheating; wherein the cooling down system is an air fan; wherein the hair appliances consist of a curling iron, a flat iron, and a hair dryer; wherein the ultraviolet lights are mercury-based lamps operating at low vapor pressure; and wherein the mercury-based lamps emit ultraviolet light at 253.7 nm.

In another embodiment of the present invention, there is a system for a UV-C light equipped smart hair appliance organizer that can be mounted on a wall with multiple push and go mounts, or taken off the wall and closed with a lid for portability; the lid containing sanitization and disinfection lights that shine ultraviolet light cm hair appliances; power outlets on the outside of the system; coiled cords connecting the hair appliances to the system; a front plate on the system that is removable such that the front plate can be replaced with another front plate containing a display screen for the purpose of advertisements; a memory coupled to a processor, the memory comprising a plurality of instructions that cause the processor to; utilize lasers in order to detect the presence of hair appliances within the wall mounted system; automatically shut off the hair appliances after a preset time period of the hair appliances being inside the system; automatically turn on ultraviolet lights for the purpose of sanitization and disinfection of the hair appliances inside the system as soon as the wall mounted system is closed; automatically shut off the ultraviolet lights after a preset time period; utilize a cooling down system in order to prevent the ultraviolet lights from overheating and in order to prevent the hair appliances from overheating; wherein the cooling down system is an air fan; wherein the hair appliances consist of a curling iron, a flat iron, and a hair dryer; wherein the ultraviolet lights are mercury-based lamps operating at low vapor pressure; and wherein the mercury-based lamps emit ultraviolet light at 253.7 nm.

In another embodiment of the invention, there is a system for a UV equipped smart hair appliance organizer that is wall mounted; a memory coupled to a processor, the memory comprising a plurality of instructions that cause the processor to: utilize lasers in order to detect the presence of hair appliances within the system; automatically shut off the hair appliances after a preset time period of the hair appliances being inside the system; automatically turn on ultraviolet lights for the purpose of sanitization and disinfection of the hair appliances inside the system as soon as the system is closed; automatically shut off the ultraviolet lights after a preset time period; and utilize a cooling down system in order to prevent the ultraviolet lights from overheating and in order to prevent the hair appliances from overheating.

In another embodiment of the invention, there is a system for a UV-C light equipped smart hair appliance organizer that is wall mounted; a memory coupled to a processor, the memory comprising a plurality of instructions that cause the processor to: utilize lasers in order to detect the presence of hair appliances within the system; automatically shut off the hair appliances after a preset time period of the hair appliances being inside the system; automatically turn on ultraviolet lights for the purpose of sterilization of the hair appliances inside the system as soon as the system is closed; automatically shut off the ultraviolet lights after a preset time period; and utilize a cooling down system in order to prevent the ultraviolet lights from overheating and in order to prevent the hair appliances from overheating.

In another embodiment of the invention, the cooling down system is an air fan.

In another embodiment of the invention, the ultraviolet lights are mercury-based lamps operating at low vapor pressure.

In another embodiment of the invention, the mercury-based lamps emit ultraviolet light at 253.7 nm.

In another embodiment of the invention, the ultraviolet lights are ultraviolet light-emitting diodes lamps.

In another embodiment of the invention, the ultraviolet lights emit ultraviolet light at selectable wavelengths between 255 and 280 nm.

In another embodiment of the invention, the ultraviolet lights are pulsed-xenon lamps, wherein the ultraviolet lights emit ultraviolet light across the entire ultraviolet spectrum with a peak emission near 230 nm.

In another embodiment of the invention, the hair appliances consist of a curling iron, a flat iron, and a hair dryer.

In another embodiment of the invention; the cords are connect to the hair appliances to the system for a UV or UV-C light equipped smart hair appliance organizer that is either wall mounted or a travel caddy are coiled cords.

In another embodiment of the invention, the cooling down system is an air fan; wherein the hair appliances consist of a curling iron, a flat iron, and a hair dryer; wherein cords connecting the hair appliances to the system for a UV or UV-C light equipped smart hair appliance organizer that is either wall mounted or a travel caddy are coiled cords; wherein the ultraviolet lights are mercury-based lamps operating at low vapor pressure; and wherein the mercury-based lamps emit ultraviolet light at 253.7 nm.

In another embodiment of the invention, a system for a UV or a UV-C light equipped smart hair appliance organizer that is either wall mounted or a travel caddy that can be mounted on a wall or taken off the wall and closed with a lid for portability; the lid containing sanitization and disinfection lights that shine ultraviolet light on hair appliances; power outlets on the outside of the system; coiled cords connecting the hair appliances to the system; a memory coupled to a processor, the memory comprising a plurality of instructions that cause the processor to: utilize lasers in order to detect the presence of hair appliances within the system; automatically shut off the hair appliances after a preset time period of the hair appliances being inside the system; automatically turn on ultraviolet lights for the purpose of sanitization and disinfection of the hair appliances inside the system as soon as the system is closed; and automatically shut off the ultraviolet lights after a preset time period.

In another embodiment of the invention, the organizer includes a drawer, wherein there are UV lights inside the drawer. A professional stylist or retail consumer can use the drawer by putting in 1 or more of a brush, comb, shears, clips and a cell phone into the drawer. Then, when the drawer is closed, the UV lights inside the drawer automatically turn on for a preselected amount of time, after which the UV lights inside the drawer turn off. This disinfects and sanitizes the products inside the drawer, such as a brush, comb, shears, clips and a cell phone.

In another embodiment of the invention, the organizer includes a drawer, wherein there are UV-C lights inside the drawer. A professional stylist or retail consumer can use the drawer by putting in 1 or more of a hair brush, hair clips comb, shears, clips, make up brushes and a cell phone into the drawer. Then, when the drawer is closed, the UV-C light lights inside the drawer automatically turn on for a preselected amount of time, after which the UV-C light lights inside the drawer turn off. This disinfects and sanitizes the products inside the drawer, such as a hair brush, make up brushes, comb, shears, clips and a cell phone and keys.

Ultraviolet (UV-C) sterilization destroys and changes the structure of microbial DNA (deoxyribonucleic acid) by ultraviolet radiation, so that the bacteria die immediately or cannot reproduce. UV sterilization has a real bactericidal effect. UVC ultraviolet rays are easily absorbed by biological DNA due to C-hand ultraviolet rays, especially about 253.7 nm.

Ultraviolet sterilization is a pure physical disinfection method. It has the advantages of being simple and convenient. It is broad-spectrum and high efficiency, such that there is no secondary pollution. Furthermore, it is easy for the user to manage, and can be adapted for automation.

In another embodiment of the invention, a system for a UV equipped smart hair appliance organizer, wherein UV sterilizer lights use highly effective UV LED beads in dual wave lengths: UVA at 395 nm and UVC at 270 nm. The UV sterilizer lights also use power of 5-8 MW. The UV sterilizer lights stay on for a time of between 20 seconds to 60 seconds. The dual wave lengths will make the light more intense, and so will sterilize more effectively. The combination of UVA and UVC light can make the sterilizer time shorter.

In another embodiment of the invention, a system for a UV-C light equipped smart hair appliance organizer, wherein UV-C sterilizer lights use highly effective UV LED beads in dual wave lengths: UVA at 395 nm and UVC at 270 nm. The sterilizer lights also use 34 power of 5-8 MW. The UV-C sterilizer lights stay on for a time of between 20 seconds to 60 seconds. The dual wave lengths will make the light more intense, and so will sterilize more effectively. The combination of UVA and UVC light can make the sterilizer time shorter.

In another embodiment of the invention, a system for a UV equipped smart hair appliance organizer, wherein UV sterilizer lights use highly effective UV LED beads in dual wave lengths: UVA at 390-405 nm and UVC at 260-270 nm. The UV sterilizer lights also use power of 5-8 MW. The UV sterilizer lights stay on for a time of between 20 seconds to 60 seconds. The dual wave lengths will make the light more intense, and so will sterilize more effectively. The combination of UVA and UVC light can make the sterilizer time shorter.

In another embodiment of the invention, a system for a UV-C light equipped smart hair appliance organizer, wherein UV-C sterilizer lights use highly effective UV LED beads in dual wave lengths: UVA at 390-405 nm and UVC at 260-270 nm. The UV-C sterilizer lights also use power of 5-8 MW. The UV-C sterilizer lights stay on for a time of between 20 seconds to 60 seconds. The dual wave lengths will make the light more intense, and so will sterilize more effectively. The combination of UVA and UVC light can make the sterilizer time shorter.

In another embodiment of the invention, a system for a UV equipped smart hair appliance organizer, wherein UV sterilizer lights use highly effective UV LED beads in dual wave lengths: UVA at 390-405 nm and UVC at 254 nm. The UV sterilizer lights also use power of 5-8 MW. The UV sterilizer lights stay on for a time of between 20 seconds to 60 seconds. The dual wave lengths will make the light more intense, and so will sterilize more effectively. The combination of UVA and UVC light can make the sterilizer time shorter. Furthermore, UVC at 254 nm has the strongest destructive power on germ genetic material, thereby increasing sterilization efficiency.

In another embodiment of the invention, a system for a UV-C light equipped smart hair appliance organizer, wherein UV-C sterilizer lights use highly effective UV-C light LED beads in dual wave lengths: UVA at 390-405 nm and UVC at 254 nm. The UV sterilizer lights also use power of 5-8 MW. The UV-C sterilizer lights stay on for a time of between 20 seconds to 60 seconds. The dual wave lengths will make the light more intense, and so will sterilize more effectively. The combination of UVA and UVC light can make the sterilizer time shorter. Furthermore, UVC at 254 nm has the strongest destructive power on germ genetic material, thereby increasing sterilization efficiency.

In another embodiment of the invention, a system for a UV equipped smart hair appliance organizer, wherein UV sterilizer lights rise highly effective UV LED beads in dual wave lengths: UVA at 390-405 nm and UVC at 253.7 nm. The UV sterilizer lights also use power of 5-8 MW. The UV sterilizer lights stay on for a time of between 20 seconds to 60 seconds. The dual wave lengths will make the light more intense, and so will sterilize more effectively. The combination of UVA and UVC light can make the sterilizer time shorter.

In another embodiment of the invention, a system for a UV-C light equipped smart hair appliance organizer, wherein UV-C sterilizer lights use highly effective UV LED beads in dual wave lengths: UVA at 390-405 nm and UVC 253.7 nm. The UV-C sterilizer lights also use power of 5-8 MW. The UV-C sterilizer lights stay on for a time of between 20 seconds to 60 seconds. The dual wave lengths will make the light more intense, and so will sterilize more effectively. The combination of UVA and UVC light can make the sterilizer time shorten.

In another embodiment of the invention, a system for a UV equipped smart hair appliance organizer, wherein UV sterilizer lights use highly effective UV LED beads in dual wave lengths: UVA at 390-405 nm and UVC at 265 nm. The UV sterilizer lights also use power of 5-8 MW. The UV sterilizer lights stay on for a time of between 20 seconds to 60 seconds. The dual wave lengths will make the light more intense, and so will sterilize more effectively. The combination of UVA and UVC light can make the sterilizer time shorter.

In another embodiment of the invention, a system for a UV-C light equipped smart hair appliance organizer, wherein UV-C sterilizer lights use highly effective UV LED beads in dual wave lengths: UVA at 390-405 nm and UVC at 265 nm. The UV-C sterilizer lights also use power of 5-8 MW. The UV-C sterilizer lights stay on for a time of between 20 seconds to 60 seconds. The dual wave lengths will make the light more intense, and so will sterilize more effectively. The combination of UVA and UVC light can make the sterilizer time shorter.

In another embodiment of the invention, a system for a UV equipped smart hair appliance organizer, wherein UV sterilizer lights use highly effective UV LED beads in dual wave lengths: UVA at 390-405 nm and UVC at 278 nm. The UV sterilizer lights also use power of 5-8 MW. The UV sterilizer lights stay on for a time of between 20 seconds to 60 seconds. The dual wave lengths will make the light more intense, and so will sterilize more effectively. The combination of UVA and UVC light can make the sterilizer time shorter.

In another embodiment of the invention, a system for a UV-C light equipped smart hair appliance organizer, wherein UV-C sterilizer lights use highly effective UV LED beads in dual wave lengths: UVA at 390-405 nm and UVC at 278 nm. The UV-C sterilizer lights also use power of 5-8 MW. The UV-C sterilizer lights stay on for a time of between 20 seconds to 60 seconds. The dual wave lengths will make the light more intense, and so will sterilize more effectively. The combination of UVA and UVC light can make the sterilizer time shorter.

In another embodiment of the invention, a system for a UV equipped smart hair appliance organizer, wherein UV sterilizer Lights use highly effective UV LED beads in dual wave lengths: UVA at 395 nm and UVC at 270 nm. The UV sterilizer lights also use power of 5-8 MW. The UV sterilizer lights stay on for a time of 2 seconds. The dual wave lengths will make the light more intense, and so will sterilize more effectively. The combination UVA and UVC light can make the sterilizer time shorter.

In another embodiment of the invention, a system for a UV-C light equipped smart hair appliance organizer, wherein UV-C sterilizer lights use highly effective UV-C light LED beads in dual wave lengths: UVA at 395 nm and UVC at 270 nm. The UV-C sterilizer lights also use power of 5-8 MW. The UV-C sterilizer lights stay on for a time of 2 seconds. The dual wave lengths will make the light more intense, and so will sterilize more effectively. The combination of UVA and UVC light can make the sterilizer time shorter.

In another embodiment of the invention, a system for a UV equipped smart hair appliance organizer, wherein UV sterilizer lights use highly effective UV LED beads in dual wave lengths: UVA at 390-405 nm and UVC at 260-270 nm. The UV sterilizer lights also use power of 5-8 MW. The UV sterilizer lights stay on for a time of 2 seconds. The dual wave lengths will make the light more intense, and so will sterilize more effectively. The combination of UVA and UVC light, can make the sterilizer time shorter.

In another embodiment of the invention, a system for a UV-C light equipped smart hair appliance organizer, wherein UV-C sterilizer lights use highly effective UV LED beads in dual wave lengths: UVA at 390-405 nm and UVC at 260-270 nm. The UV-C sterilizer lights also use power of 5-8 MW. The UV-C sterilizer lights stay on for a time of 2 seconds. The dual wave lengths will make the light more intense, and so will sterilize more effectively. The combination of UVA and UVC light can make the sterilizer time shorter.

In another embodiment of the invention, a system for a UV equipped smart hair appliance organizer, wherein UV sterilizer lights use highly effective UV LED beads in dual wave lengths: UVA at 390-405 nm and UVC at 253.7 nm. The UV sterilizer lights also use power of 5-8 MW. The UV sterilizer lights stay on for a time of 2 seconds. The dual wave lengths will make the light more intense, and so will sterilize more effectively. The combination of UVA and UVC light can make the sterilizer time shorter.

In another embodiment of the invention, a system for a UV-C light equipped smart hair appliance, organizer, wherein UV-C sterilizer lights use highly of UV LED beads in dual wave lengths: UVA at 390-405 nm and UVC at 253.7 nm. The UV-C sterilizer lights also use power of 5-8 MW. The UV-C sterilizer lights stay on for a time of 2 seconds. The dual wave lengths will make the light more intense, and so will sterilize more effectively. The combination of UVA and UVC light can make the sterilizer time shorter.

In another embodiment of the invention, a system for a UV equipped smart hair appliance organizer, wherein UV sterilizer lights use highly effective UV LED beads in dual wave lengths: UVA at 390-405 nm and UVC at 265 nm. The UV sterilizer lights also use power of 5-8 MW. The UV sterilizer lights stay on for a time of 2 seconds. The dual wave lengths will make the light more intense, and so will sterilize more effectively. The combination of UVA and UVC light can make the sterilizer time shorter.

In another embodiment of the invention, a system for a UV-C light equipped smart hair appliance organizer, wherein UV sterilizer lights use highly effective UV-C light LED heads in dual wave lengths: UVA at 390-405 nm and UVC at 265 nm. The UV-C sterilizer lights also use power of 5-8 MW. The UV-C sterilizer lights stay on for a time of 2 seconds. The dual wave lengths will make the light more intense, and so will sterilize more effectively. The combination of UVA and UVC light can make the sterilizer time shorter.

In another embodiment of the invention, a system for a UV equipped smart hair appliance organizer, wherein UV sterilizer lights rise highly effects UV LED beads in dual wave lengths: UVA at 390-405 nm and UVC at 278 nm. The UV sterilizer lights also use power of 5-8 MW. The UV sterilizer lights stay on for a time of between 2 seconds. The dual wave lengths will make the light more intense, and so will sterilize more effectively. The combination of UVA and UVC light can make the sterilizer time shorter.

In another embodiment of the invention, a system for a UV-C light equipped smart hair appliance organizer, wherein UV sterilizer lights use highly effective UV-C light LED beads in dual wave lengths; UVA at 390-405 nm and UVC at 278 nm. The UV-C sterilizer lights also use power of 5-8 MW. The UV-C sterilizer lights stay on for a time of between 2 seconds. The dual wave lengths will make the light more intense, and so will sterilize more effectively. The combination of UVA and UVC light can make the sterilizer time shorter.

In another embodiment of the invention, there are 2 UVC light sterilizer boards in a curling iron holding compartment, 4 UVC sterilizer light boards in a flat iron compartment, and 2 sterilizer light boards in a blow dryer holding compartment. There is also 1 sterilizer light board in the top part of the drawer.

In another embodiment of the invention, the UV-C lights sterilize the hair appliances in the holding compartments, and cosmetologists' shears, clips, combs and brushes in the drawer.

In another embodiment of the invention, the UVC lights are on a 3 minute cycle before turning off for each hair appliance compartment and the drawer. However, testing in a lab environment indicated that sterilization occurred in 20-60 seconds. Setting a 3 minute cycle is just extra precautionary to make sure the sterilization is complete.

In another embodiment of the invention, the UV-C lights will last 20,000 hours before they will burn out.

In another embodiment of the invention, the UV-C light equipped smart hair appliance organizer housing is composed of a plastic shell, and custom electronic components built from scratch. The main electronic components include: a motherboard, a power board, infrared sensors, sockets, control IC Chips, relays and UVC sterilizing LED boards in each hair appliance compartment and in the drawer.

The left side of the organizer has a power button and power plugs for a blow dryer, flat iron and curling iron. The back of the organizer has All of the components are put together utilizing soldering, so as to make the organizer stable.

There are 3 relays in the motherboard that connect to three sockets. The motherboard connects to every UVC sterilizer board. The Motherboard has a control IC chip, so it can control each group of UVC sterilizer boards which work for the different hair appliances in each holding compartment. There are infrared sensors in every UVC sterilizer board.

For example, for the hair dryer compartment:

There are two UVC sterilizer boards put face to face to sterilize the hair dryer nozzle. One UVC sterilizer board with infrared induction emission, and another one with an infrared sensor receiver. When the hair dryer is placed back in the holding compartment, it will stop the infrared sensor receiver, the control IC Chip will then begin working making the UVC light activate and turn on for 3 minutes to sterilize the hair dryer. After 3 minutes the relay will stop the power for the socket and turn off the UVC light sterilizer boards. You can pull the hair dryer out of the holding compartment at any time, and the Infrared sensor will activate, and the control IC chip relay will supply power to the socket, so the hair dryer can have power to turn on the moment the hair dryer is pulled out of the holding compartment.

For example, for the curling iron compartment:

There are two UVC sterilizer boards put face to face, to sterilize the curling iron barrel. One with Infrared induction emission, and another one with an infrared sensor receiver. When the curling iron is placed back in the holding compartment, it will stop the infrared sensor receiver, the control IC Chip will then begin working making the UVC light activate and turn on for 3 minutes to sterilize the curling iron barrel. The curling iron power will remain active with power for 2 hours from the last time the curling iron barrel was placed in the curling iron holding compartment. After 2 hours from last time the curling iron barrel was placed in the curling iron compartment the relay will stop the power for the socket which connects with curling iron. When you pull the curling iron out of the holding compartment, the Infrared sensor will activate, and the control IC chip relay will supply power to the socket so the curling iron can have power to turn on again the moment the curling iron is pulled out of the holding compartment.

For example, for the Flat iron Compartment:

There are 4 UVC sterilizer board put face to face, to sterilize the flat iron barrel. One with Infrared induction emission, and another one with an infrared sensor receiver. When the flat iron is placed back, in the holding compartment, it will stop the infrared sensor receiver, the control IC Chip will then begin working making the UVC light activate and turn on for 3 minutes to sterilize the flat iron barrel. The flat iron power will remain active with power for 2 hours from the last time the flat iron barrel was placed in the flat iron bolding compartment. After 2 hours from last time the flat iron barrel was placed in the flat iron compartment the relay will stop the power for the socket which connects with curling iron. When you pull the flat iron out of the holding compartment, the Infrared sensor will activate, and the control IC chip relay will supply power to the socket so the flat iron can, have power to turn on again the moment the flat iron is pulled out of the holding compartment.

In another embodiment of the invention, regarding the 2 hour auto shut off feature for the curling iron and flat iron: when a user puts the curling iron and flat iron in the holding compartments, the UVC Lights activate for 3 minutes, and relays will still supply power to the socket for 2 hours. If 2 hours pass without the curling iron or flat iron being removed from the holding compartment, the power supply to the sockets will be stopped creating a 2 hour auto shut off system. The moment the flat iron or ending iron are pulled out of the holding compartments, the power is immediately activated so the curling iron and flat iron power will resume. If the flat iron or curling iron is pulled out of the holding compartment anytime less than 2 hours, then a 2 hour timer will reset starting the auto shut off cycle again.

The blow dryer has an immediate auto shut off, and immediate power on feature: The principle is the moment you place the blow dryer nozzle in the blow dryer holding compartment with the blow dryer motor power on, the blow dryer power will be shut off, shutting the blow dryer power and motor down immediately. Then moment the blow dryer is pulled out of the blow dryer holding compartment the blow dryer power and blow dryer motor will turn on immediately.

The UVC sterilization light board is on top. When a user takes out the UVC equipped drawer the IR. Sensor begins detection. After a user puts the UVC equipped drawer in the organizer, the IR sensor detects the presence of an object in the drawer, and the control IC chip makes the UVC sterilizer light activate for 3 minutes.

In another embodiment of the invention, there is a strap for traveling, the strap connects to D rings, which connect to the organizer. The strap allows a user to more comfortably travel with the organizer.

In another embodiment of the invention designed for professionals, there is a back bracket that allows the organizer to release from the wall. The bracket has 2 parts: Part A and a part B. Part A is glued or screwed onto the wall. Part B pan is screwed onto the organizer. A user can release the organizer from the wall by lifting the organizer, which is attached to part B, off of part A, which is attached to the wall.

In another embodiment of the invention designed for a hotel, there is a back bracket is for permanent mounting of the organizer, so that hotel guests cannot move the organizer from the hotel wall. The organizer mounts permanently to the hotel bathroom wall. The back bracket has 1 part, and it is glued or screwed onto the wall directly.

In another embodiment of the invention, a UVC equipped drawer has the following dimensions: Width: 274.2 mm, Face height; 98.45 mm, Back height 85.5 mm.

In another embodiment of the invention, there is a UVC Equipped Lid for the professional model and the hotel model. The UVC Equipped Lid is equipped with UVC light boards on top. The UVC lid connects to the organizer with a USB cable that connects the organizer with a USB port. This UVC lid sterilizes the handles, and all top exposed areas of the hair appliances. When a user closes the UVC lid and connects the USB port, UVC lights from the UVC light boards will activate for 3 minutes.

In another embodiment of the invention, there are 4 extremely strong suction cups on the bottom corners of the organizer. This will allow the organizer to be placed on most hard surfaces, and hold a suction to the surface so the unit will not tip over. In our testing, you can use a large amount of force by pushing, pulling and shoving when the unit is placed on a most hard surfaces, and the organizer will not tip over and remain upright and attached onto the hard surfaces we tested.

In another embodiment of the invention, there are 2 cord wrap knobs on the right side of the organizer so the user can wrap the Blow Dryer, Flat Iron and Curling iron cords when they travel with the unit.

In another embodiment of the invention, there is a system, comprising: an ultraviolet equipped organizer for hair appliances ("organizer") that can be mounted on a wall or taken off the wall; wherein there are three circular holes on the top of the organizer, wherein each hole has a board inside the hole on the side of the hole wherein one hole has the circumference of a hair dryer, another hole has the circumference of a curling iron, and another hole has the circumference of a flat iron; wherein each hoard contains sanitization and disinfecting lights that shine ultraviolet light on hair appliances; wherein one side of each hole contains an infrared induction emission, and the other side of each hole contains an infrared sensor receiver; a drawer containing sanitization and disinfecting lights that shine ultraviolet light on hair appliances; power outlets on the outside of the organizer; coiled cords connecting the hair appliances to the organizer; a memory coupled to a processor, the memory comprising a plurality of instructions that cause the processor to: utilize each infrared induction emission and infrared sensor receiver in each hole in order to detect the presence of hair appliances within each hole in the organizer; determine if the hair appliances are on and inside the organizer, and if so automatically shut off the hair appliances after a preset time period of the hair appliances being inside the organizer; automatically turn on ultraviolet lights for the purpose of sanitization and disinfection of the hair appliances inside the organizer as soon as the organizer is closed; and automatically shut off the ultraviolet lights after a preset time period; wherein a front plate on the ultraviolet equipped hair appliance organizer is removable such that the front plate can be replaced with another front plate containing a display screen for the purpose of advertisements and selling products; wherein the ultraviolet lights are ultraviolet light-emitting diodes lamps; wherein the ultraviolet lights emit in dual wave lengths, both ultraviolet A light and ultraviolet C light; wherein the ultraviolet lights emit ultraviolet A light at the wavelength 395 nm; wherein the ultraviolet lights emit ultraviolet C light at the wavelengths 270 nm; wherein the ultraviolet lights use power between 5 and 8 megawatts (MW); wherein the ultraviolet lights stay on between 20 and 60 seconds; and wherein the ultraviolet light creates an inhospitable environment for bacteria and viruses.

In another embodiment of the invention, a system, comprising: an ultraviolet equipped organizer for hair appliances ("organizer") that can be mounted on a wall or taken off the wall; wherein there are three circular holes on the top of the organizer, wherein each hole has a board inside the hole on a side of the hole; wherein one hole has the circumference of a hair dryer, another hole has the circumference of a curling iron, and another hole has the circumference of a flat iron; wherein each board contains sanitization and disinfecting lights that shine ultraviolet light on hair appliances; wherein the hair appliances consist of a curling iron, a flat iron, and a hair dryer; wherein one side of each hole contains an infrared induction emission, and the other side of each hole contains an infrared sensor receiver; a drawer containing sanitization and disinfecting lights that shine ultraviolet light on hair appliances; power outlets on the outside of the organizer; coiled cords connecting the hair appliances to the organizer; a memory coupled to a processor, the memory comprising a plurality of instructions that cause the processor to: utilize each infrared induction emission and infrared sensor receiver in each hole in order to detect the presence of hair appliances within each hole in the organizer; determine if the hair appliances are on and inside the organizer, and if so automatically shut off the hair appliances after a preset time period of the hair appliances being inside the organizer; utilize an air fan for cooling, down both the organizer and the hair appliances in order to prevent the ultraviolet lights from overheating and in order to prevent the hair appliances from overheating; automatically turn on ultraviolet lights for the purpose of sanitization and disinfection of the hair appliances inside the organizer as soon as the organizer is closed; and automatically shut off the ultraviolet lights after a preset time period; wherein the ultraviolet lights are ultraviolet light-emitting diodes lamps; wherein the ultraviolet lights emit in dual wave lengths, both ultraviolet A light and ultraviolet C light; wherein the ultraviolet lights emit ultraviolet A light at selectable wavelengths between 390 and 405 nm; wherein the ultraviolet lights emit ultraviolet C light at selectable wavelengths between 260 and 270 nm; wherein the ultraviolet lights use power between 5 and 8 megawatts (MW); wherein the ultraviolet lights stay on between 20 and 60 seconds; and wherein the ultraviolet light creates an inhospitable environment for bacteria and viruses.

In another embodiment of the invention, the depth of each hole is 196 mm.

In another embodiment of the invention, a front plate on the ultraviolet equipped hair appliance organizer is removable such that the front plate can be replaced with another front plate containing a display screen for the purpose of advertisements and selling products.

In another embodiment of the invention, there is a system, comprising: an ultraviolet equipped organizer for hair appliances ("organizer") that can be mounted on a wall or taken off the wall; wherein there are three circular holes on the top of the organizer, wherein each hole has a board inside the hole on a side of the hole; wherein one hole has the circumference of a hair dryer, another hole has the circumference of a curling iron, and another hole has the circumference of a flat iron; wherein each board contains sanitization and disinfecting lights that shine ultraviolet light on hair appliances; wherein the hair appliances consist of a curling iron, a flat iron, and a hair dryer; wherein one side of each hole contains an infrared induction emission, and the other side of each hole contains an infrared sensor receiver; a drawer containing sanitization and disinfecting lights that shine ultraviolet light on hair appliances; power outlets on the outside of the organizer; coiled cords connecting the hair appliances to the organizer; a memory coupled to a processor, the memory comprising a plurality of instructions that cause the processor to: utilize each infrared induction emission and infrared sensor receiver in each hole in order to detect the presence of hair appliances within each hole in the organizer: determine if the hair appliances are on and inside the organizer, and if so automatically shut off the hair appliances after a preset time period of the hair appliances being inside the organizer; utilize an air fan for cooling down both the organizer and the hair appliances in order to prevent the ultraviolet lights from overheating and in order to prevent the hair appliances from overheating; automatically turn on ultraviolet lights for the purpose of sanitization and disinfection of the hair appliances inside the organizer as soon as the organizer is closed; and automatically shut off the ultraviolet lights after a preset time period; wherein the ultraviolet lights are ultraviolet light emitting diodes; wherein the ultraviolet lights emit in dual wave lengths, both ultraviolet A light and ultraviolet C light; wherein the ultraviolet lights emit ultraviolet A light at selectable wavelengths between 390 and 405 nm; wherein the ultraviolet lights emit ultraviolet C light at the wavelengths 254 nm; wherein the ultraviolet lights use power between 5 and 8 megawatts (MW); wherein the ultraviolet lights stay on for 2 seconds; and wherein the ultraviolet light creates an inhospitable environment for bacteria and viruses.

In another embodiment of the invention, there is a system, comprising: an ultraviolet equipped organizer for hair appliances ("organizer") that can be mounted on a wall or taken off the wall; wherein there are three circular holes on the top of the organizer, wherein each hole has a board inside the bole on each side of the hole; wherein each board contains sanitization and disinfecting lights that shine ultraviolet light on hair appliances; wherein one side of each hole contains an infrared induction emission, and the other side of each hole contains an infrared sensor receiver; a drawer containing sanitization and disinfecting lights that shine ultraviolet light on hair appliances; power outlets on the outside of the organizer; a memory coupled to a processor, the memory comprising a plurality of instructions that cause the processor to: utilize each infrared induction emission and infrared sensor receiver in each hole in order to detect the presence of hair appliances within each hole organizer; utilize an air fan for cooling down both the organizer and the hair appliances in order to prevent the ultraviolet lights from overheating and in order to prevent the hair appliances from overheating; automatically turn on ultraviolet lights for the purpose of sanitization and disinfection of the hair appliances inside the organizer as soon as the organizer is closed; and automatically shut off the ultraviolet lights after a preset time period; wherein the ultraviolet lights are ultraviolet light-emitting diodes lamps; wherein the ultraviolet lights emitting dual wave lengths, both ultraviolet A light and ultraviolet C light; wherein the ultraviolet lights emit ultraviolet A light at selectable wavelengths between 390 and 405 nm; wherein the ultraviolet lights emit ultraviolet C light at selectable wavelengths between 260 and 270 nm; wherein the ultraviolet lights use power between 5 and 8 megawatts (MW); wherein the ultraviolet lights stay on between 20 and 60 seconds; and wherein the ultraviolet light creates an inhospitable environment for bacteria and viruses.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document) in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic news described in this specification can be performed by one or more programmable processors executing one or more computer programs to perform actions by operating on input data and generating output. The processes and logic flows can also be performed by, and apparatus can also be implemented as, special purpose logic circuitry, e.g., FPGA (field programmable gate array) or an ASIC (application-specific integrated circuit).

Generally, a processor will receive instructions and data from a read-only memory or a random access memory or both. The essential elements of a computer are a processor for performing actions in accordance with instructions and one or more memory devices for storing instructions and data. Generally, computer will also include, or be operatively coupled to receive data from or transfer data to, or both, one or more mass storage devices for storing data e.g., magnetic, magneto-optical disks, or optical disks. However, a computer need not have such devices. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display), LED (light emitting diode), or OLED (organic light emitting diode) monitor, for displaying information to the user and a keyboard and a pointing device, e.g., a mouse or a trackball, by which the user can provide input to the computer. In some implementations, a touch screen can be used to display information and to receive input from a user. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user'S client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

From the foregoing, it will be appreciated that specific embodiments or the invention have been described herein for purposes of illustration, but that various modifications may be made without deviating from the spirit and scope of the invention. Accordingly, the invention is not limited except as by the appended claims.

The invention claimed is:

1. A system, comprising:
an ultraviolet equipped organizer for hair appliances ("organizer");
that can be mounted on a wall or taken off the wall;
wherein there are three circular holes on the top of the organizer, wherein each hole has a board inside the hole on the side of the hole;
wherein one hole has the circumference of a hair dryer, another hole has the circumference of a curling iron, and another hole has the circumference of a flat iron;
wherein each board contains sanitization and disinfecting lights that shine ultraviolet light on hair appliances;
wherein one side of each hole contains an infrared induction emission, and the other side of each hole contains an infrared sensor receiver;
a drawer containing sanitization and disinfecting lights that shine ultraviolet light on hair appliances;
power outlets on the outside of the organizer;
coiled cords connecting the hair appliances to the organizer;
a memory coupled to a processor, the memory comprising a plurality of instructions that cause the processor to:
utilize each infrared induction emission and infrared sensor receiver in each hole in order to detect the presence of hair appliances within each hole in the organizer;
determine if the hair appliances are on and inside the organizer, and if so automatically shut off the hair appliances after a preset time period of the hair appliances being inside the organizer;
automatically turn on ultraviolet lights for the purpose of sanitization and disinfection of the hair appliances inside the organizer as soon as the organizer is closed; and
automatically shut off the ultraviolet lights after a preset time period;
wherein a front plate on the ultraviolet equipped hair appliance organizer is removable such that the front plate can be replaced with another front plate containing a display screen for the purpose of advertisements and selling products;
wherein the ultraviolet lights are ultraviolet light-emitting diodes lamps; wherein the ultraviolet lights emit in dual wave lengths, both ultraviolet A light and ultraviolet C light;
wherein the ultraviolet lights emit ultraviolet A light at the wavelength 395 nm;
wherein the ultraviolet lights emit ultraviolet C light at the wavelengths 270 nm;
wherein the ultraviolet lights use power between 5 and 8 megawatts (MW);
wherein the ultraviolet lights stay on between 20 and 60 seconds; and
wherein the ultraviolet light creates an inhospitable environment for bacteria and viruses.

2. A system, comprising:
an ultraviolet equipped organizer for hair appliances ("organizer");
that can be mounted on a wall or taken off the wall;

wherein there are three circular holes on the top of the organizer, wherein each hole has a board inside the hole on a side of the hole;
wherein one hole has the circumference of a hair dryer, another hole has the circumference of a curling iron, and another hole has the circumference of a flat iron;
wherein each board contains sanitization and disinfecting lights that shine ultraviolet light on hair appliances;
wherein the hair appliances consist of a curling iron, a flat iron, and a hair dryer;
wherein one side of each hole contains an infrared induction emission, and the other side of each hole contains an infrared sensor receiver;
a drawer containing sanitization and disinfecting lights that shine ultraviolet light on hair appliances;
power outlets on the outside of the organizer;
coiled cords connecting the hair appliances to the organizer;
a memory coupled to a processor, the memory comprising a plurality of instructions that cause the processor to:
utilize each infrared induction emission and infrared sensor receiver in each hole in order to detect the presence of hair appliances within each hole in the organizer;
determine if the hair appliances are on and inside the organizer, and if so automatically shut off the hair appliances after a preset time period of the hair appliances being inside the organizer;
utilize an air fan for cooling down both the organizer and the hair appliances in order to prevent the ultraviolet lights from overheating and in order to prevent the hair appliances from overheating;
automatically turn on ultraviolet lights for the purpose of sanitization and disinfection of the hair appliances inside the organizer as soon as the organizer is closed; and
automatically shut off the ultraviolet lights after a preset time period;
wherein the ultraviolet lights are ultraviolet light-emitting diodes lamps; wherein the ultraviolet lights emit in dual wave lengths, both ultraviolet A light and ultraviolet C light;
wherein the ultraviolet lights emit ultraviolet A light at selectable wavelengths between 390 and 405 nm;
wherein the ultraviolet lights emit ultraviolet C light at selectable wavelengths between 260 and 270 nm;
wherein the ultraviolet lights use power between 5 and 8 megawatts (MW);
wherein the ultraviolet lights stay on between 20 and 60 seconds; and
wherein the ultraviolet light creates an inhospitable environment for bacteria and viruses.

3. The system of claim 2, further comprising:
wherein the depth of each hole is 196 mm.

4. The system of claim 2, further comprising:
wherein a front plate on the ultraviolet equipped hair appliance organizer is removable such that the front plate can be replaced with another front plate containing a display screen for the purpose of advertisements and selling products.

5. A system, comprising:
an ultraviolet equipped organizer for hair appliances ("organizer");
that can be mounted on a wall or taken off the wall;
wherein there are three circular holes on the top of the organizer, wherein each hole has a board inside the hole on a side of the hole;
wherein one hole has the circumference of a hair dryer, another hole has the circumference of a curling iron, and another hole has the circumference of a flat iron;
wherein each board contains sanitization and disinfecting lights that shine ultraviolet light on hair appliances;
wherein the hair appliances consist of a curling iron, a flat iron, and a hair dryer;
wherein one side of each hole contains an infrared induction emission, and the other side of each hole contains an infrared sensor receiver;
a drawer containing sanitization and disinfecting lights that shine ultraviolet light on hair appliances;
power outlets on the outside of the organizer;
coiled cords connecting the hair appliances to the organizer;
a memory coupled to a processor, the memory comprising a plurality of instructions that cause the processor to:
utilize each infrared induction emission and infrared sensor receiver in each hole in order to detect the presence of hair appliances within each hole in the organizer;
determine if the hair appliances are on and inside the organizer, and if so automatically shut off the hair appliances after a preset time period of the hair appliances being inside the organizer;
utilize an air fan for cooling down both the organizer and the hair appliances in order to prevent the ultraviolet lights from overheating and in order to prevent the hair appliances from overheating;
automatically turn on ultraviolet lights for the purpose of sanitization and disinfection of the hair appliances inside the organizer as soon as the organizer is closed; and
automatically shut off the ultraviolet lights after a preset time period;
wherein the ultraviolet lights are ultraviolet light emitting diodes;
wherein the ultraviolet lights emit in dual wave lengths, both ultraviolet A light and ultraviolet C light;
wherein the ultraviolet lights emit ultraviolet A light at selectable wavelengths between 390 and 405 nm;
wherein the ultraviolet lights emit ultraviolet C light at the wavelengths 254 nm;
wherein the ultraviolet lights use power between 5 and 8 megawatts (MW);
wherein the ultraviolet lights stay on for 2 seconds; and
wherein the ultraviolet light creates an inhospitable environment for bacteria and viruses.

6. A system, comprising:
an ultraviolet equipped organizer for hair appliances ("organizer");
that can be mounted on a wall or taken off the wall;
wherein there are three circular holes on the top of the organizer, wherein each hole has a board inside the hole on each side of the hole;
wherein each board contains sanitization and disinfecting lights that shine ultraviolet light on hair appliances;
wherein one side of each hole contains an infrared induction emission, and the other side of each hole contains an infrared sensor receiver;
a drawer containing sanitization and disinfecting lights that shine ultraviolet light on hair appliances;
power outlets on the outside of the organizer;
a memory coupled to a processor, the memory comprising a plurality of instructions that cause the processor to:

utilize each infrared induction emission and infrared sensor receiver in each hole in order to detect the presence of hair appliances within each hole in the organizer;

utilize an air fan for cooling down both the organizer and the hair appliances in order to prevent the ultraviolet lights from overheating and in order to prevent the hair appliances from overheating;

automatically turn on ultraviolet lights for the purpose of sanitization and disinfection of the hair appliances inside the organizer as soon as the organizer is closed; and automatically shut off the ultraviolet lights after a preset time period;

wherein the ultraviolet lights are ultraviolet light-emitting diodes lamps; wherein the ultraviolet lights emit in dual wave lengths, both ultraviolet A light and ultraviolet C light;

wherein the ultraviolet lights emit ultraviolet A light at selectable wavelengths between 390 and 405 nm;

wherein the ultraviolet lights emit ultraviolet C light at selectable wavelengths between 260 and 270 nm;

wherein the ultraviolet lights use power between 5 and 8 megawatts (MW);

wherein the ultraviolet lights stay on between 20 and 60 seconds; and wherein the ultraviolet light creates an inhospitable environment for bacteria and viruses.

\* \* \* \* \*